US012558029B2

(12) United States Patent
Phillips et al.

(10) Patent No.: US 12,558,029 B2
(45) Date of Patent: Feb. 24, 2026

(54) SIMULTANEOUS BLOOD GLUCOSE MONITORING AND GASTRIC EMPTYING SCINTIGRAPHY

(71) Applicant: The Board of Regents of the University of Texas System, Austin, TX (US)

(72) Inventors: William T. Phillips, Austin, TX (US); Brandon Gorzell, Austin, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1149 days.

(21) Appl. No.: 17/310,945

(22) PCT Filed: Mar. 11, 2020

(86) PCT No.: PCT/US2020/022025
§ 371 (c)(1),
(2) Date: Sep. 1, 2021

(87) PCT Pub. No.: WO2020/185857
PCT Pub. Date: Sep. 17, 2020

(65) Prior Publication Data
US 2022/0183586 A1 Jun. 16, 2022

Related U.S. Application Data

(60) Provisional application No. 62/841,378, filed on May 1, 2019, provisional application No. 62/817,342, filed on Mar. 12, 2019.

(51) Int. Cl.
*A61B 5/00* (2006.01)
*A61B 5/145* (2006.01)
(Continued)

(52) U.S. Cl.
CPC ........ *A61B 5/4866* (2013.01); *A61B 5/14532* (2013.01); *A61B 5/42* (2013.01);
(Continued)

(58) Field of Classification Search
CPC ................. A61B 5/14532; A61B 5/42; A61B 5/4211–4216; A61B 5/4238;
(Continued)

(56) References Cited

U.S. PATENT DOCUMENTS 5,159,081 A * 10/1992 Cantrell ................. A61P 25/04
546/233
9,498,155 B2 * 11/2016 Brauker ............. A61B 5/14532
(Continued)

FOREIGN PATENT DOCUMENTS

WO 2017201538 A1 11/2017

OTHER PUBLICATIONS

International Search Report and Written Opinion issued on Jun. 11, 2020 in PCT International Application No. PCT/US2020/022025.
(Continued)

*Primary Examiner* — Tse W Chen
*Assistant Examiner* — Alice Ling Zou
(74) *Attorney, Agent, or Firm* — Amster, Rothstein & Ebenstein LLP

(57) ABSTRACT

Systems and methods are provided for providing improved information, diagnoses and therapies for dyspepsia and gastric emptying disorders based on gastric protein emptying and gastric carbohydrate emptying data.

7 Claims, 16 Drawing Sheets

(51) Int. Cl.
    *A61B 6/40*          (2024.01)
    *A61B 6/50*          (2024.01)

(52) U.S. Cl.
    CPC .......... *A61B 5/4839* (2013.01); *A61B 5/7264*
        (2013.01); *A61B 5/746* (2013.01); *A61B*
        *6/4057* (2013.01); *A61B 5/7445* (2013.01);
              *A61B 6/50* (2013.01)

(58) Field of Classification Search
    CPC ...... A61B 5/4255; A61B 5/4836–4839; A61B
        5/7445; A61B 6/12; A61B 6/4057; A61B
        6/486; A61B 6/50; A61B 5/4866; A61B
        5/746; A61B 6/4258; A61B 5/7275; A61P
        1/00; A61P 1/14; A61P 3/08–10; A61K
        49/0004; A61K 51/1296; G01N
                 2800/0426
    See application file for complete search history.

(56)             References Cited

U.S. PATENT DOCUMENTS

2004/0215068 A1* 10/2004 Lykke ................... A61B 5/062
                                 600/302
2005/0020931 A1*  1/2005 Ben-Oren .......... A61K 49/0004
                                 424/9.1
2005/0059704 A1*  3/2005 Landau ................... A61P 43/00
                                 514/338
2008/0281166 A1* 11/2008 Bush ................... A61B 6/4258
                                 600/300
2012/0269865 A1* 10/2012 Roughead ................ A61P 1/04
                                 426/74
2013/0030503 A1   1/2013 Yaniv et al.
2014/0379267 A1* 12/2014 Williams ........... A61K 49/0004
                                 702/19
2015/0343144 A1* 12/2015 Altschul .............. A61B 5/4839
                                 604/503
2017/0080207 A1   3/2017 Perez et al.
2017/0169725 A1*  6/2017 Cahan ................ A61B 5/14532

OTHER PUBLICATIONS

McWhorter et al., Simultaneous Blood Glucose Monitoring During Gastric-Emptying Scintigraphy May Identify Unsuspected Abnormalities, Clinical Nuclear Medicine, vol. 43, No. 6, Jun. 2018, pp. 411-419.
Ramzan et al., Continuous Glucose Monitoring in Gastroparesis, Digestive Diseases and Sciences, vol. 56, Jul. 7, 2011, pp. 2646-2655.

* cited by examiner

SOLID GASTRIC EMPTYING WORKSHEET

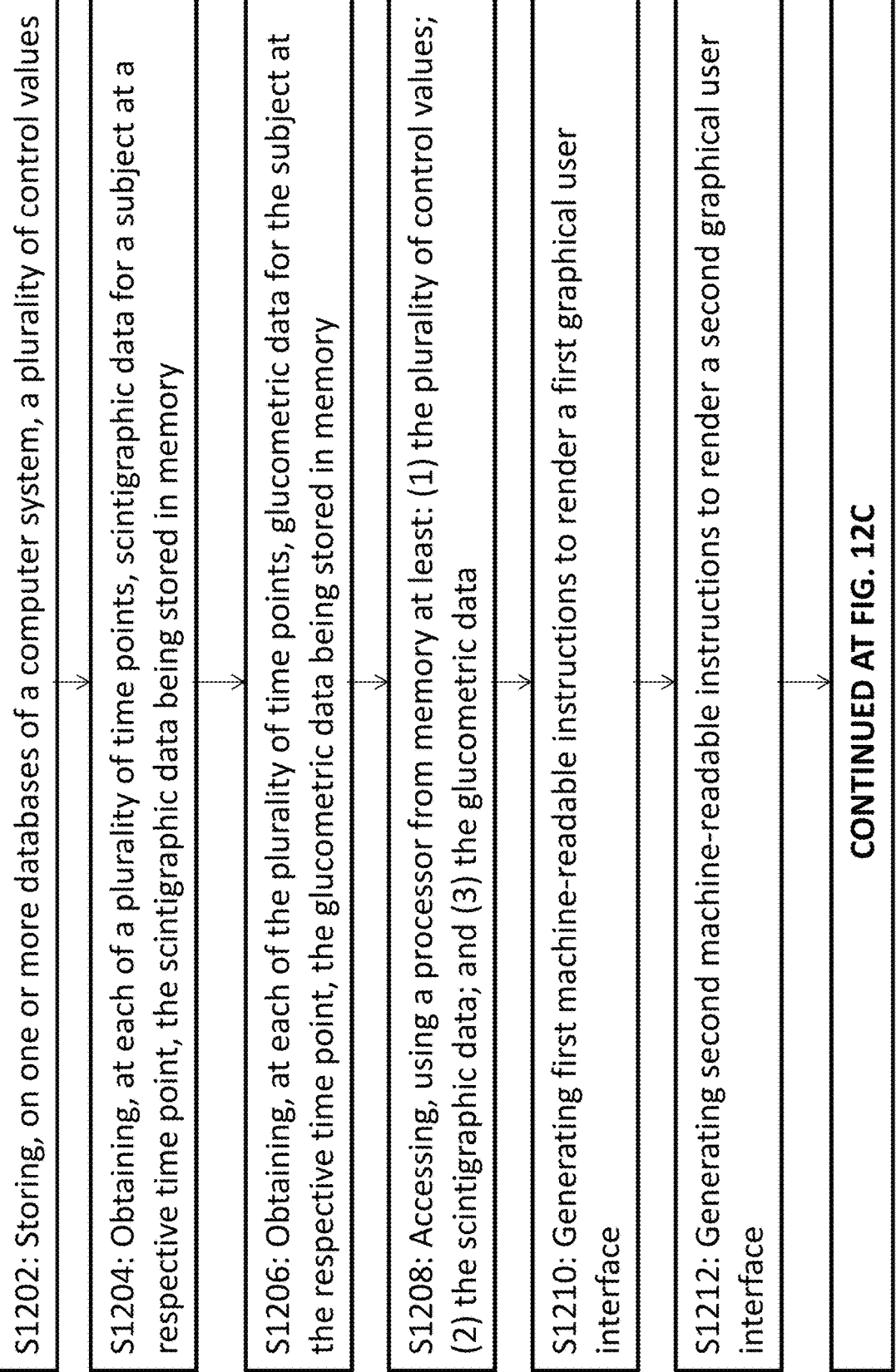

S1202: Storing, on one or more databases of a computer system, a plurality of control values S1204: Obtaining, at each of a plurality of time points, scintigraphic data for a subject at a respective time point, the scintigraphic data being stored in memory S1206: Obtaining, at each of the plurality of time points, glucometric data for the subject at the respective time point, the glucometric data being stored in memory S1208: Accessing, using a processor from memory at least: (1) the plurality of control values; (2) the scintigraphic data; and (3) the glucometric data S1210: Generating first machine-readable instructions to render a first graphical user interface S1212: Generating second machine-readable instructions to render a second graphical user interface

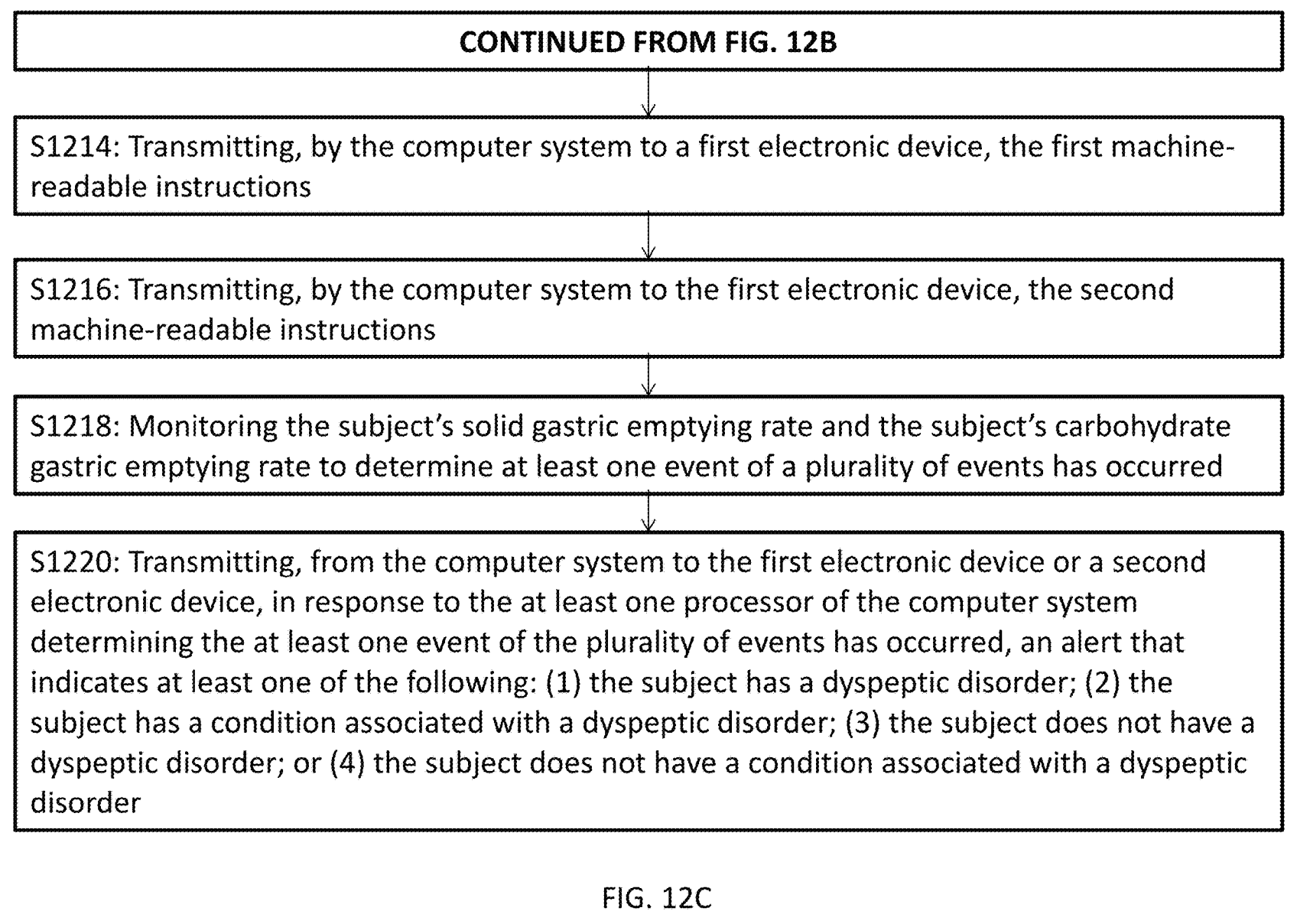

CONTINUED FROM FIG. 12B

↓

S1214: Transmitting, by the computer system to a first electronic device, the first machine-readable instructions

↓

S1216: Transmitting, by the computer system to the first electronic device, the second machine-readable instructions

↓

S1218: Monitoring the subject's solid gastric emptying rate and the subject's carbohydrate gastric emptying rate to determine at least one event of a plurality of events has occurred

↓

S1220: Transmitting, from the computer system to the first electronic device or a second electronic device, in response to the at least one event of the plurality of events has occurred, an alert that indicates at least one of the following: (1) the subject has a dyspeptic disorder; (2) the subject has a condition associated with a dyspeptic disorder; (3) the subject does not have a dyspeptic disorder; or (4) the subject does not have a condition associated with a dyspeptic disorder

FIG. 12C

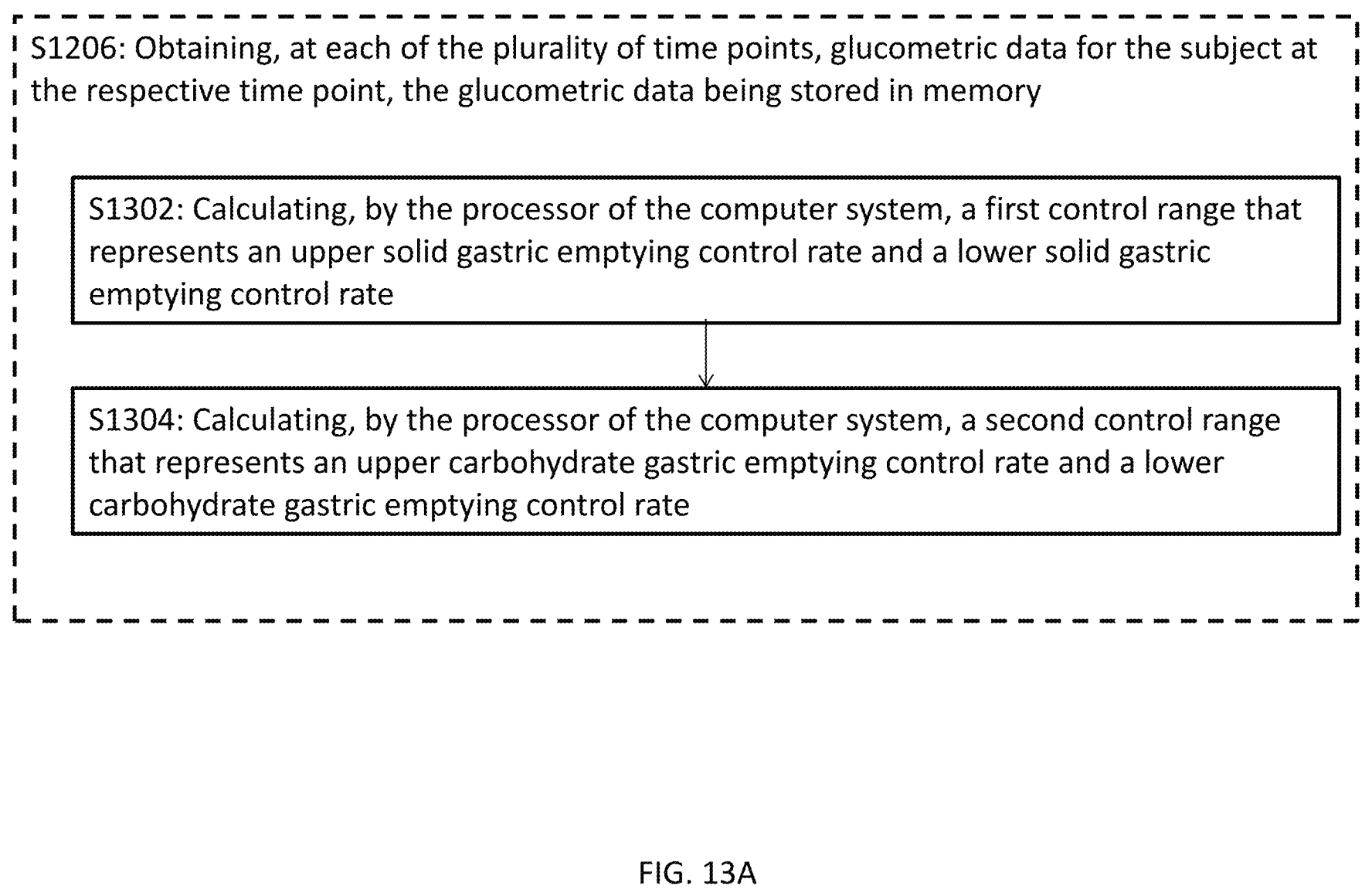

S1206: Obtaining, at each of the plurality of time points, glucometric data for the subject at the respective time point, the glucometric data being stored in memory S1302: Calculating, by the processor of the computer system, a first control range that represents an upper solid gastric emptying control rate and a lower solid gastric emptying control rate S1304: Calculating, by the processor of the computer system, a second control range that represents an upper carbohydrate gastric emptying control rate and a lower carbohydrate gastric emptying control rate

FIG. 13A

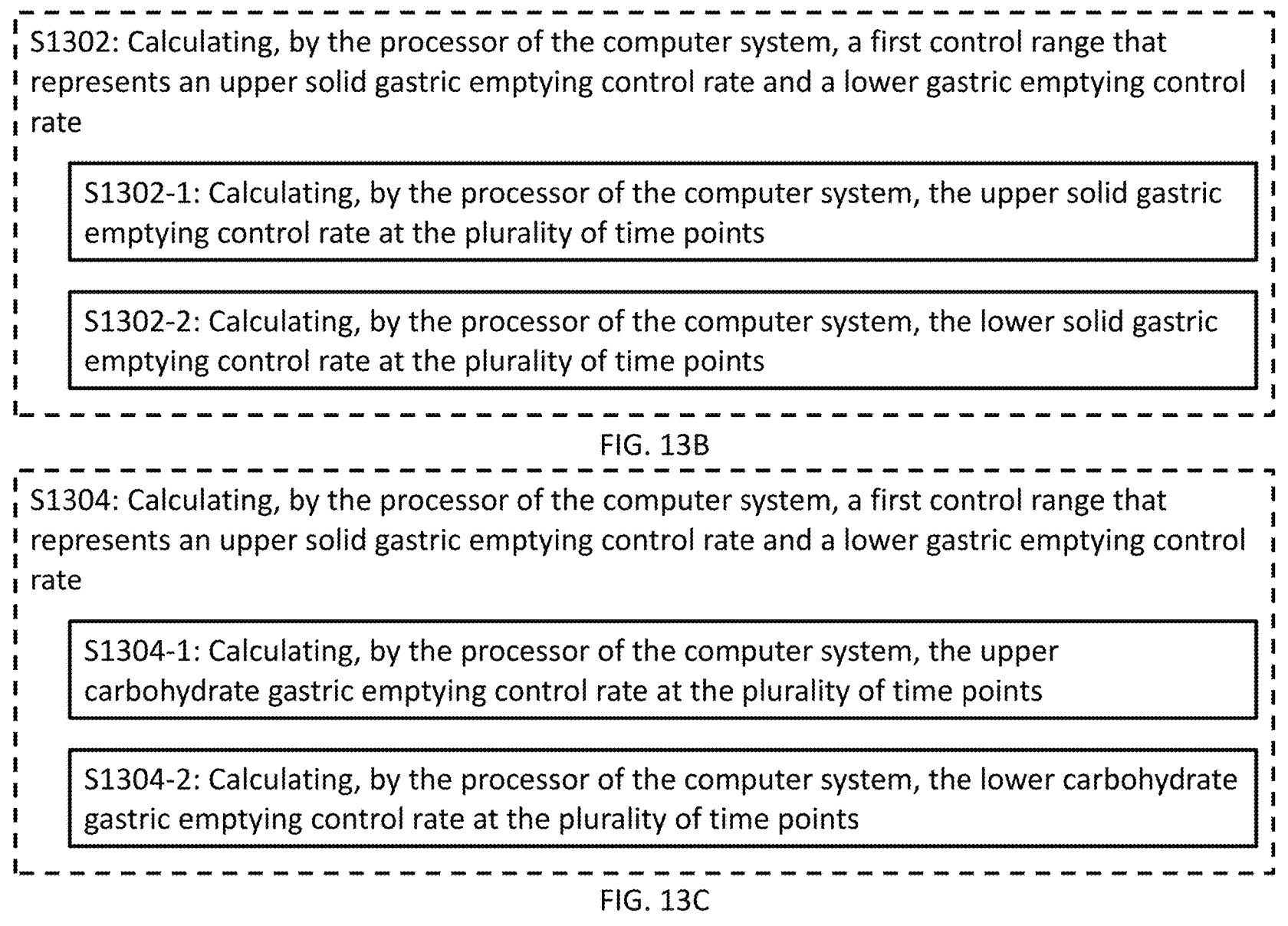

S1302: Calculating, by the processor of the computer system, a first control range that represents an upper solid gastric emptying control rate and a lower gastric emptying control rate S1302-1: Calculating, by the processor of the computer system, the upper solid gastric emptying control rate at the plurality of time points S1302-2: Calculating, by the processor of the computer system, the lower solid gastric emptying control rate at the plurality of time points

FIG. 13B

S1304: Calculating, by the processor of the computer system, a first control range that represents an upper solid gastric emptying control rate and a lower gastric emptying control rate S1304-1: Calculating, by the processor of the computer system, the upper carbohydrate gastric emptying control rate at the plurality of time points S1304-2: Calculating, by the processor of the computer system, the lower carbohydrate gastric emptying control rate at the plurality of time points

FIG. 13C

SIMULTANEOUS BLOOD GLUCOSE MONITORING AND GASTRIC EMPTYING SCINTIGRAPHY

CROSS-REFERENCE TO RELATED APPLICATIONS

This application is a U.S. national stage entry under 35 U.S.C. § 371 of PCT International Patent Application No. PCT/US2020/022025, filed Mar. 11, 2020, which claims benefit of U.S. Provisional Application No. 62/817,342, filed Mar. 12, 2019 and of U.S. Provisional Application No. 62/841,378 filed May 1, 2019, the contents of each of which are hereby incorporated by reference.

FIELD

The field of the invention generally relates to various technological improvements in systems, methods, and program products used in correct diagnosis and complete classification/diagnosis of gastric emptying disorders and related conditions, as well as treatment of diagnosis of gastric emptying disorders and related conditions.

BACKGROUND OF THE INVENTION

Throughout this application various publications are referred to, including by number(s) in square brackets and by number(s) in parenthesis. Full citations for these references may be found at the end of the specification. The disclosures of these publications, and all patents, patent application publications and books referred to herein, are hereby incorporated by reference in their entirety into the subject application to more fully describe the art to which the subject invention pertains.

The standardized solid radiolabeled egg-white gastric emptying study has been widely adopted for assessment of gastric emptying abnormalities. The standardization of gastric emptying studies alleviated the considerable confusion of study interpretation posed by a wide variety of clinical gastric emptying meals, and thereby facilitated a true comparison between patients in different institutions and on repeat study (1). In the standardized gastric emptying meal, egg-white is radiolabeled with $^{99m}$TC-sulfur colloid (SC) and combined with two pieces of toast and strawberry jam. The most commonly used meals in clinical gastric emptying scintigraphy (GES) radiolabel the protein component of a mixed meal (1, 5, 6). However, current GES methods provide partial information that lead to misdiagnosis and incomplete classification/diagnosis of gastric emptying disorders and related conditions. These errors can result in inappropriate and/or deleterious administered therapies based on the misdiagnosis or incomplete classification/diagnosis. What is needed is technological improvements in systems, methods, and program products for correct diagnosis and complete classification/diagnosis of gastric emptying disorders and related conditions, as well as treatment of diagnosis of gastric emptying disorders and related conditions.

SUMMARY OF THE INVENTION

An object of the present invention to address one or more of the above medical technological problems as outlined in the prior art.

The field of the invention generally relates to various technological improvements in systems, methods, and program products used in correct diagnosis and complete classification/diagnosis of gastric emptying disorders and related conditions, as well as treatment of diagnosis of gastric emptying disorders and related conditions.

In embodiments, a system for classifying gastric emptying in a subject, may comprise: a) a scintigraphic measurement equipment configured to measure, from a subject that has ingested at a set time point a meal comprising carbohydrate and radiolabeled protein, scintigraphic data of the subject's solid gastric emptying rate at a plurality of time points over a predetermined amount of time, subsequent to the set time point; b) a glucometric measurement equipment configured to measure, from the subject, glucometric data of the subject's blood glucose level at the plurality of time points subsequent to the set time point; c) a computer system, comprising at least one processor and computer readable memory operatively connected to the at least one processor, which computer system is operatively connected to the scintigraphic measurement equipment and the glucometric measurement equipment, and wherein the computer system is configured to perform the steps of: (1) storing on the memory a plurality of control values in one or more databases, wherein the plurality of control values comprise: (A) a first set of solid gastric emptying control values, wherein each solid gastric emptying control value of the first set of solid gastric emptying control values corresponds to one time point of the plurality of time points, and wherein for a first set of time points of the plurality of time points, the first set of solid gastric emptying control values comprises at least one of (1) a predetermined upper solid gastric emptying value and (2) a predetermined lower solid gastric emptying value; and (B) a second set of blood glucose control values, wherein each blood glucose control value of the second set of blood glucose control values corresponds to one time point of the plurality of time points, and wherein for a second set of time points of the plurality of time points, the second set of blood glucose control value corresponds to at least one of (1) a predetermined upper blood glucose value, and (2) a predetermined lower blood glucose value; (2) at each of the plurality of time points, performing the following steps: obtaining, from the scintigraphic measurement equipment, at a respective time point respective scintigraphic data for the subject, and storing said respective time point and said respective scintigraphic data in memory; (i) obtaining, from the glucometric measurement equipment, at the respective time point respective glucometric data for the subject, and storing said respective time point and said respective glucometric data in memory; (ii) accessing, using the processor from memory, for at least the respective time point, at least the following respective time point information: a. respective scintigraphic data; b. respective predetermined upper solid gastric emptying value to the extent available; c. respective predetermined lower solid gastric emptying value to the extent available; d. respective glucometric data; e. respective predetermined upper blood glucose value to the extent available; f. respective predetermined lower blood glucose value to the extent available; (iv) generating, by the computer system, first machine-readable instructions to render a first graphical user interface including a first graphical representation of: a. the scintigraphic data for the subject at the respective time point; b. the predetermined upper solid gastric emptying value at the respective time point, to the extent available; and c. the predetermined lower solid gastric emptying value at the respective time point, to the extent available; and (v) generating, by the computing system, second machine-readable instructions to render a second graphical user interface including a second graphical representation of: a. the glucometric data for the subject at the respective time point; b. the predetermined upper blood glucose value, at the respective time point, to the extent available; and c. the predetermined lower blood glucose value at the respective time point, to the extent available; d) transmitting, by the computer system to a first electronic device, the first machine-readable instructions so as to cause the first electronic device to render the first graphical user interface on a first screen of a display associated with the first electronic device comprising a visual display of the subject's solid gastric emptying rate; e) transmitting by the computer system to the first electronic device, the second machine-readable instructions so as to cause the first electronic device to render the second graphical user interface on a second screen of the display associated with the first electronic device comprising a visual display of the subject's blood glucose levels; f) monitoring, by the at least one processor of the computer system, the subject's solid gastric emptying rate and of the subject's blood glucose levels to determine at least one event of a plurality of events has occurred, wherein the plurality of events includes: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; (ix) delayed gastric solid emptying at 2 hours postprandial and delayed blood glycemic excursion; (x) normal gastric solid emptying and elevated blood glycemic excursion; (xi) normal gastric solid emptying and delayed blood glycemic excursion; and (xii) normal gastric solid emptying and normal blood glycemic excursion; g) transmitting, from the computer system to the first electronic device or a second electronic device, in response to the at least one processor of the computer system determining the at least one event of the plurality of events has occurred, an alert wherein the alert indicates that the subject has a dyspeptic disorder, or as having a condition associated with a dyspeptic disorder, if the at least one event is one or more of f)(i) through f)(xi), and wherein the alert indicates that the subject does not have a dyspeptic disorder or a condition associated with a dyspeptic disorder if the at least one event is f)(xii).

In embodiments, also provided is a system for classifying gastric emptying in a subject, comprising: a) a first scintigraphic measurement equipment configured to measure, from a subject that has ingested at a set time point a meal comprising carbohydrate and radiolabeled protein, first scintigraphic data of the subject's protein solid gastric emptying rate at a plurality of time points over a predetermined amount of time, subsequent to the set time point; b) a second scintigraphic measurement equipment configured to measure, from the subject, second scintigraphic data of carbohydrate gastric emptying at the plurality of time points subsequent to the set time point; c) a computer system, comprising at least one processor and computer readable memory operatively connected to the at least one processor, which computer system is operatively connected to the first scintigraphic measurement equipment and the second scintigraphic measurement equipment, and wherein the computer system is configured to perform the steps of: (1) storing on the memory a plurality of control values in one or more databases, wherein plurality of control values comprise: (A) a first set of protein solid gastric emptying control values, wherein each protein solid gastric emptying control value of the first set of protein solid gastric emptying control values corresponds to one time point of the plurality of time points, and wherein for a first set of time points of the plurality of time points, the first set of protein solid gastric emptying control values comprises at least one of (1) a predetermined upper protein solid gastric emptying value and (2) a predetermined lower protein solid gastric emptying value; and (B) a second set of carbohydrate gastric emptying control values, wherein each carbohydrate gastric emptying control value of the second set of carbohydrate gastric emptying control values corresponds to one time point of the plurality of time points, and wherein for a second set of time points of the plurality of time points, the second set of carbohydrate gastric emptying control values corresponds to at least one of (1) a predetermined upper carbohydrate gastric emptying level value, and (2) a predetermined lower carbohydrate gastric emptying level value; (2) at each of the plurality of time points, performing the following steps: (i) obtaining, from the first scintigraphic measurement equipment, at a respective time point respective first scintigraphic data for the subject, and storing said respective time point and said respective first scintigraphic data in memory; (ii) obtaining, from the second scintigraphic measurement equipment, at the respective time point respective second scintigraphic data for the subject, and storing said respective time point and said respective second scintigraphic data in memory; (iii) accessing, using the processor from memory, for at least the respective time point, at least the following respective time point information: a. respective first scintigraphic data; b. respective predetermined upper protein solid gastric emptying value to the extent available; c. respective predetermined lower protein solid gastric emptying value to the extent available; d. respective second scintigraphic data; e. respective predetermined upper carbohydrate gastric emptying value to the extent available; f. respective predetermined lower carbohydrate gastric emptying value to the extent available; (iv) generating, by the computer system, first machine-readable instructions to render a first graphical user interface including a first graphical representation of: a. the first scintigraphic data for the subject at the respective time point; b. the predetermined upper protein solid gastric emptying value at the respective time point, to the extent available; and c. the predetermined lower protein solid gastric emptying value at the respective time point, to the extent available; and (v) generating, by the computing system, second machine-readable instructions to render a second graphical user interface including a second graphical representation of: a. the second scintigraphic data for the subject at the respective time point; b. the predetermined upper carbohydrate gastric emptying value, at the respective time point, to the extent available; and c. the predetermined lower carbohydrate gastric emptying value at the respective time point, to the extent available; d) transmitting, by the computer system to a first electronic device, the first machine-readable instructions so as to cause the first electronic device to render a graphical user interface on a first screen of a display associated with the first electronic device comprising a visual display of the subject's protein solid gastric emptying rate; e) transmitting by the computer system to the first electronic device, the second machine-readable instructions so as to cause the first electronic device to render a graphical user interface on a second screen of the display associated with the first electronic device comprising a visual display of the subject's carbohydrate gastric emptying rate; f) monitoring, by the at least one processor of the computer system, the subject's protein solid gastric emptying rate and of the subject's blood glucose level rate to determine at least one event of a plurality of events has occurred, wherein the plurality of events includes: (i) rapid gastric solid emptying and rapid carbohydrate gastric emptying; (ii) rapid gastric solid emptying and normal carbohydrate gastric emptying; (iii) rapid gastric solid emptying and delayed carbohydrate gastric emptying; (iv) delayed gastric solid emptying at 4 hours postprandial and delayed carbohydrate gastric emptying; (v) delayed gastric solid emptying at 2 hours postprandial and normal carbohydrate gastric emptying; (vi) delayed gastric solid emptying at 2 hours postprandial and delayed carbohydrate gastric emptying; (vii) delayed gastric solid emptying at 2 hours postprandial and rapid carbohydrate gastric emptying; (viii) delayed gastric solid emptying at 2 hours postprandial and normal carbohydrate gastric emptying; (ix) delayed gastric solid emptying at 2 hours postprandial and delayed carbohydrate gastric emptying; (x) normal gastric solid emptying and rapid carbohydrate gastric emptying; (xi) normal gastric solid emptying and delayed carbohydrate gastric emptying; and (xii) normal gastric solid emptying and normal carbohydrate gastric emptying; g) transmitting, from the computer system to the first electronic device or a second electronic device, in response to the at least one processor of the computer system determining the at least one event of the plurality of events has occurred, an alert wherein the alert indicates that the subject has a dyspeptic disorder, or as having a condition associated with a dyspeptic disorder, if the at least one event is one or more of f)(i) through f)(xi), and wherein the alert indicates that the subject does not have a dyspeptic disorder or a condition associated with a dyspeptic disorder if the at least one event is f)(xii).

In embodiments, also provided is a system for diagnosing a subject as having a dyspeptic disorder, or as having a condition associated with a dyspeptic disorder, or for classifying gastric emptying in a subject as one of twelve different classifications, comprising: a) obtaining, from a subject that has ingested at a set time point a meal comprising carbohydrate and radiolabeled protein: (i) scintigraphic data of the subject's solid gastric emptying rate at a plurality of time points subsequent to the set time point; and (ii) glucometric data of the subject's blood glucose level at a plurality of time points subsequent to the set time point; b) integrating, using a processor, the scintigraphic data and glucometric data to provide, respectively, a measurement of solid gastric emptying rate and carbohydrate gastric emptying rate in the subject; c) listing and/or plotting on a visual display the measurement of solid gastric emptying rate and carbohydrate gastric emptying rate compared to at least a first control value for solid gastric emptying rate and compared to at least a second control value for carbohydrate gastric emptying in a standard subject; d) sending an alert to a user of the system indicating the subject as having a dyspeptic disorder, or as having a condition associated with a dyspeptic disorder, when the solid gastric emptying rate and/or carbohydrate gastric emptying in the subject varies from the corresponding control value by a predetermined amount.

In embodiments, also provided is a system for diagnosing a subject as having a dyspeptic disorder, or as having a condition associated with a dyspeptic disorder, or for classifying gastric emptying in a subject as one of twelve different classifications, comprising: a) obtaining, from a subject that has ingested at a set time point a meal comprising a radiolabeled carbohydrate and radiolabeled protein, a first scintigraphic data set of the subject's carbohydrate gastric emptying rate and a second scintigraphic data set of protein gastric emptying rate at a plurality of time points subsequent to the set time point; b) integrating, using a processor, the first and second scintigraphic data sets to provide, respectively, a measurement of carbohydrate gastric emptying rate and a measurement of solid gastric emptying rate and in the subject; c) listing and/or plotting on a visual display the measurement of solid gastric emptying rate and carbohydrate gastric emptying rate compared to at least a first control value for solid gastric emptying rate and compared to at least a second control value for carbohydrate gastric emptying in a standard subject; d) sending an alert to a user of the system indicating the subject as having a dyspeptic disorder, or as having a condition associated with a dyspeptic disorder, when the solid gastric emptying rate and/or carbohydrate gastric emptying in the subject varies from the corresponding control value by a predetermined amount.

In embodiments, also provided d is a method of treating a subject for a condition associated with a gastric emptying disorder comprising determining which gastric emptying disorder the subject has using a system described herein and administering to the subject a medication for that gastric emptying disorder.

In embodiments, also provided is a method of prophylactically treating a subject against a condition associated with a gastric emptying disorder comprising determining which gastric emptying disorder the subject has using the system described herein and administering to the subject a prophylactic medication for delaying or reducing development of the condition.

In embodiments, also provided is a method of diagnosing a subject as having a dyspeptic disorder, or as having a condition associated with a dyspeptic disorder, or for classifying gastric emptying in a subject as one of twelve different classifications, comprising quantitatively determining, simultaneously, a carbohydrate gastric emptying rate and a protein gastric emptying rate of the subject and plotting on a visual display a measurement of protein gastric emptying rate compared to at least two different first control values and a carbohydrate gastric emptying rate compared to at least two different second control values wherein the control values are set from a standard subject; receiving an alert as a user of the system indicating the subject as having a dyspeptic disorder, or as having a condition associated with a dyspeptic disorder, when the solid gastric emptying rate and/or carbohydrate gastric emptying in the subject varies from any of the corresponding control values by a predetermined amount, and thereby diagnosing a subject as having a dyspeptic disorder, or as having a condition associated with a dyspeptic disorder, or for classifying gastric emptying in a subject as one of twelve different classifications.

In embodiments, also provided is a method of obtaining differentiation of protein and carbohydrate gastric emptying rates in a subject, comprising quantitatively determining a carbohydrate gastric emptying rate and a protein gastric emptying rate of the subject and plotting on a visual display a measurement of protein gastric emptying rate compared to at least two different first control values and a carbohydrate gastric emptying rate compared to at least two different second control values wherein the control values are set from a standard subject; classifying gastric emptying in a subject as one of twelve different classifications from the following: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; (ix) delayed gastric solid emptying at 2 hours postprandial and delayed blood glycemic excursion; (x) normal gastric solid emptying and elevated blood glycemic excursion; (xi) normal gastric solid emptying and normal blood glycemic excursion; or (xii) normal gastric solid emptying and delayed blood glycemic excursion, so as to thereby obtain differentiation of protein and carbohydrate gastric emptying rates in a subject.

BRIEF DESCRIPTION OF THE DRAWINGS

The above and related objects, features, and advantages of the present invention, will be more fully understood by reference to the following detailed description of the exemplary embodiments of the present invention, when taken in conjunction with the following exemplary figures, wherein:

Referring to FIG. 12A, an exemplary computer system 1202 in communication with exemplary scintigraphic measurement equipment 1214, exemplary glucometric measurement equipment 1212, an exemplary first electronic device 1218 and/or an exemplary second electronic device 1228 via network 1216. The network 1216 may be the Internet, an intranet network, a local area network, other wireless or other hardwired connection or connections, or a combination of one or more thereof, by which individual components of the system may communicate. In embodiments, the computer system 1202, the scintigraphic measurement equipment 1214, the glucometric measurement equipment 1212, the first electronic device 1218 and/or the second electronic device 1228 may include personal computers and/or mobile devices, such as cellphones, smartwatches, other smart wearable devices, exercise equipment with user interfaces, and the like, with Internet access that are uniquely identifiable by Internet Protocol (IP) addresses, Internet cookies, Media Access Control (MAC) identifiers, or online personal accounts of the individual users, corporations, and/or organizations associated with the computer system 1202, the scintigraphic measurement equipment 1214, the glucometric measurement equipment 1212, the first electronic device 1218 and/or the second electronic device 1228, either directly or through another electronic device.

FIGS. 12B and 12C: Flow charts of a process for determining whether a subject has a dyspeptic disorder or a condition associated with a dyspeptic disorder. The process described in connection with FIGS. 12B and 12C may be performed by a system for classifying gastric emptying in a subject (e.g., the system described in connection with FIG. 12A). In embodiments, the process described in connection with FIGS. 12B and 12C may begin with providing the scintigraphic measurement equipment 1214, which may be configured to measure scintigraphic data of the subject's 1238 solid gastric emptying rate at a plurality of time points over a predetermined amount of time. The subject 1238, in embodiments and subsequent to the set time point, may have ingested at a set time point a meal. The meal, in embodiments, may include carbohydrate and radiolabeled protein.

FIG. 13A: The sub-process of step S1206 may continue at a step S1304. At step S1304, processor(s) 1204 may calculate the second control range. The second control range, may represent an upper carbohydrate gastric emptying control rate and a lower carbohydrate gastric emptying control rate. This calculation, may be performed by the process illustrated in the flow chart shown in connection with FIG. 13C.

FIGS. 13B and 13C: 13B) Flowchart—at step S1302-1, the processor(s) 1204 may calculate the upper solid gastric emptying control rate at the plurality of time points of the predetermined amount of time. The upper limit, in embodiments, may represent the upper limit of a healthy solid gastric emptying rate of the subject 1238. The upper limit may be determined and/or calculated as discussed herein. Continuing the calculations, at step S1302-2, the processor(s) 1204 may calculate the lower solid gastric emptying control rate at the plurality of time points of the predetermined amount of time. The lower limit, in embodiments, may represent the lower limit of a healthy solid gastric emptying rate of the subject 1238. The lower limit may be determined and/or calculated as discussed herein. 13C) At step S1304-1, the processor(s) 1204 may calculate the upper carbohydrate gastric emptying control rate at the plurality of time points of the predetermined amount of time. The upper limit, in embodiments, may represent the upper limit of a healthy carbohydrate gastric emptying rate of the subject 1238. The upper limit may be determined and/or calculated as discussed herein. Continuing the calculations, at step S1304-2, the processor(s) 1204 may calculate the lower carbohydrate gastric emptying control rate at the plurality of time points of the predetermined amount of time. The lower limit, in embodiments, may represent the lower limit of a healthy carbohydrate gastric emptying rate of the subject 1238. The lower limit may be determined and/or calculated as discussed herein.

DETAILED DESCRIPTION OF THE INVENTION

Figure 1:
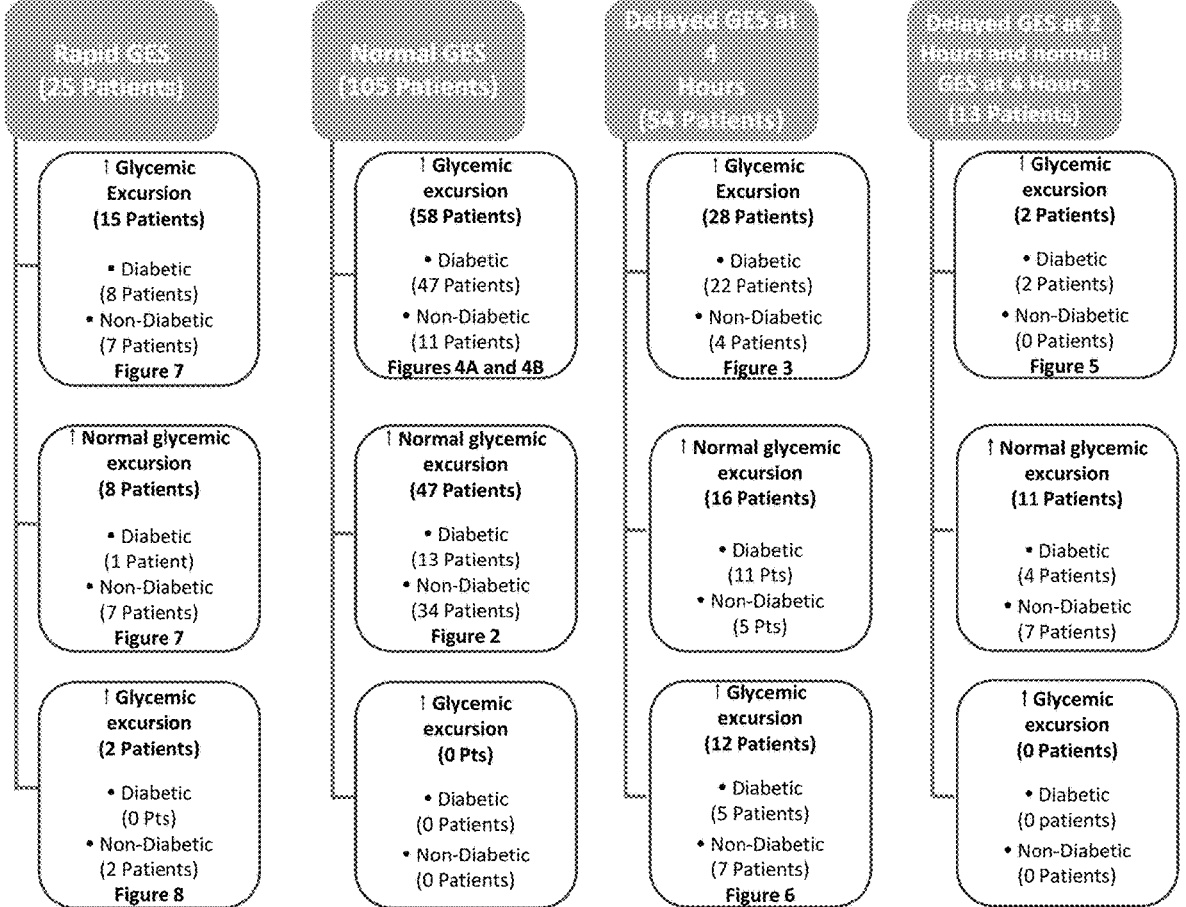
FIG. 1: Graph showing the classification of 197 patients with rapid, normal and delayed solid emptying which are further classified into those with elevated, normal or diminished postprandial glycemic excursions during the first postprandial hour in patients with and without diabetes. Examples in typical patients in some of the categories above are shown FIGS. 2-8.

The field of the invention generally relates to various technological improvements in systems, methods, and program products used in correct diagnosis and complete classification/diagnosis of gastric emptying disorders and related conditions, as well as treatment of diagnosis of gastric emptying disorders and related conditions.

Embodiments of the present invention described herein avoids the prior art issues of misdiagnosis and incomplete classification/diagnosis of gastric emptying disorders and related conditions. These errors resulting from prior art systems can lead to inappropriate and/or deleterious administered therapies based on the misdiagnosis or incomplete classification/diagnosis, for example, administration of pro-motility drugs to a subject when there is little to no motility deficit. In addition, the increased layering and diversification of gastric emptying information the systems provide results in less time needed to perform diagnosis, classification and/or initiation of appropriate therapy which reduces the total amount of patient discomfort, improves efficiency of use of hospital facilities and staffing, and increases the resolution of gastric emptying classification to at least twelve different classes.

In embodiments, a system is provided for classifying gastric emptying in a subject, comprising: a) a scintigraphic measurement equipment configured to measure, from a subject that has ingested at a set time point a meal comprising carbohydrate and radiolabeled protein, scintigraphic data of the subject's solid gastric emptying rate at a plurality of time points over a predetermined amount of time, subsequent to the set time point; b) a glucometric measurement equipment configured to measure, from the subject, glucometric data of the subject's blood glucose level at the plurality of time points subsequent to the set time point; c) a computer system, comprising at least one processor and computer readable memory operatively connected to the at least one processor, which computer system is operatively connected to the scintigraphic measurement equipment and the glucometric measurement equipment, and wherein the computer system is configured to perform the steps of: (1) storing on the memory a plurality of control values in one or more databases, wherein plurality of control values comprise: (A) a first set of solid gastric emptying control values, wherein each solid gastric emptying control value of the first set of solid gastric emptying control values corresponds to one time point of the plurality of time points, and wherein for a first set of time points of the plurality of time points, the first set of solid gastric emptying control values comprises at least one of (1) a predetermined upper solid gastric emptying value and (2) a predetermined lower solid gastric emptying value; and (B) a second set of blood glucose control values, wherein each blood glucose control value of the second set of blood glucose control values corresponds to one time point of the plurality of time points, and wherein for a second set of time points of the plurality of time points, the second set of blood glucose control value corresponds to at least one of (1) a predetermined upper blood glucose value, and (2) a predetermined lower blood glucose value; (2) at each of the plurality of time points, performing the following steps: (i) obtaining, from the scintigraphic measurement equipment, at a respective time point respective scintigraphic data for the subject, and storing said respective time point and said respective scintigraphic data in memory; (ii) obtaining, from the glucometric measurement equipment, at the respective time point respective glucometric data for the subject, and storing said respective time point and said respective glucometric data in memory; (iii) accessing, using the processor from memory, for at least the respective time point, at least the following respective time point information: a. respective scintigraphic data; b. respective predetermined upper solid gastric emptying value to the extent available; c. respective predetermined lower solid gastric emptying value to the extent available; d. respective glucometric data; e. respective predetermined upper blood glucose value to the extent available; f. respective predetermined lower blood glucose value to the extent available; (iv) generating, by the computer system, first machine-readable instructions to render a first graphical user interface including a first graphical representation of: a. the scintigraphic data for the subject at the respective time point; b. the predetermined upper solid gastric emptying value at the respective time point, to the extent available; and c. the predetermined lower solid gastric emptying value at the respective time point, to the extent available; and (v) generating, by the computing system, second machine-readable instructions to render a second graphical user interface including a second graphical representation of: a. the glucometric data for the subject at the respective time point; b. the predetermined upper blood glucose value, at the respective time point, to the extent available; and c. the predetermined lower blood glucose value at the respective time point, to the extent available; d) transmitting, by the computer system to a first electronic device, the first machine-readable instructions so as to cause the first electronic device to render the first graphical user interface on a first screen of a display associated with the first electronic device comprising a visual display of the subject's solid gastric emptying rate; e) transmitting by the computer system to the first electronic device, the second machine-readable instructions so as to cause the first electronic device to render the second graphical user interface on a second screen of the display associated with the first electronic device comprising a visual display of the subject's blood glucose levels; f) monitoring, by the at least one processor of the computer system, the subject's solid gastric emptying rate and of the subject's blood glucose levels to determine at least one event of a plurality of events has occurred, wherein the plurality of events includes: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; (ix) delayed gastric solid emptying at 2 hours postprandial and delayed blood glycemic excursion; (x) normal gastric solid emptying and elevated blood glycemic excursion; (xi) normal gastric solid emptying and delayed blood glycemic excursion; and (xii) normal gastric solid emptying and normal blood glycemic excursion; g) transmitting, from the computer system to the first electronic device or a second electronic device, in response to the at least one processor of the computer system determining the at least one event of the plurality of events has occurred, an alert wherein the alert indicates that the subject has a dyspeptic disorder, or as having a condition associated with a dyspeptic disorder, if the at least one event is one or more of f)(i) through f)(xi), and wherein the alert indicates that the subject does not have a dyspeptic disorder or a condition associated with a dyspeptic disorder if the at least one event is f)(xii).

In embodiments, provided is a system is provided for diagnosing a subject as having a dyspeptic disorder, or as having a condition associated with a dyspeptic disorder, or for classifying gastric emptying in a subject as one of twelve different classifications, comprising: a) obtaining, from a subject that has ingested at a set time point a meal comprising carbohydrate and radiolabeled protein: (i) scintigraphic data of the subject's solid gastric emptying rate at a plurality of time points subsequent to the set time point; and (ii) glucometric data of the subject's blood glucose level at a plurality of time points subsequent to the set time point; b) integrating, using a processor, the scintigraphic data and glucometric data to provide, respectively, a measurement of solid gastric emptying rate and carbohydrate gastric emptying rate in the subject; c) listing and/or plotting on a visual display the measurement of solid gastric emptying rate and carbohydrate gastric emptying rate compared to at least a first control value for solid gastric emptying rate and compared to at least a second control value for carbohydrate gastric emptying in a standard subject; d) sending an alert to a user of the system indicating the subject as having a dyspeptic disorder, or as having a condition associated with a dyspeptic disorder, when the solid gastric emptying rate and/or carbohydrate gastric emptying in the subject varies from the corresponding control value by a predetermined amount. In embodiments, the system is for diagnosing a subject as having a dyspeptic disorder. In embodiments, the system is for diagnosing a subject as having a condition associated with a dyspeptic disorder. In embodiments, the system is for classifying gastric emptying in a subject as one of twelve different classifications.

Dyspeptic disorders include the disorder commonly known as indigestion, gastroparesis, and functional dyspepsia. Conditions associated with dyspeptic disorders are known in the art and include gastroesophageal reflux disease, ulcers, or gallbladder disease. Dyspepsia is often experienced as a persistent or recurrent pain or discomfort in the upper abdomen and may be accompanied by other gastrointestinal symptoms.

In embodiments of the systems or methods, the alert is unique for each of one of nine different categories of dyspeptic disorder, or of the condition associated with a dyspeptic disorder.

In embodiments of the systems or methods, the scintigraphic data comprises mean geometric amount of $^{99m}$Tc-sulfur colloid movement quantified from a user-determined region of interest the subject. In embodiments of the system, the $^{99m}$Tc-sulfur colloid has been ingested by the subject in the meal comprising carbohydrate and radiolabeled protein. Other ingestible radiolabels may be used to label the protein containing meal.

In embodiments of the systems or methods, a baseline amount of radiolabel activity in a user-determined region of interest of the subject is determined at, or immediately after, ingestion of the meal and is obtained as scintigraphic data using a gamma camera.

In embodiments of the systems or methods, the carbohydrate gastric emptying rate is calculated from subject blood glycemic excursions measured by a glucometer.

In embodiments of the systems or methods, the glucometric data is obtained using a glucose biosensor, wherein the glucose biosensor is hexokinase, glucose oxidase (GOx) or glucose-1-dehydrogenase (GDH) based.

In embodiments of the systems or methods, (i) the first control value and/or second control value are normalized for total kilocalorie amount of meal ingested by subject, and/or (ii) the second control value is normalized for subject's fasting glucose level.

In embodiments of the systems or methods, a subject is indicated as having a dyspeptic disorder, or as having a condition associated with a dyspeptic disorder, when the solid gastric emptying rate is >30% emptying by 0.5 hours after subject has ingested a radiolabeled protein meal and/or >70% emptying by 1.0 hours after subject has ingested a radiolabeled protein meal.

In embodiments of the systems or methods, the alert sent to the user indicates that the subject has rapid gastric solid emptying.

In embodiments of the systems or methods, a subject is indicated as having a dyspeptic disorder, or as having a condition associated with a dyspeptic disorder, when the solid gastric emptying rate is (i)<90% emptying by 4 hours after subject has ingested a radiolabeled protein meal or (ii)

(a)<10% emptying by 1.0 hours after subject has ingested a radiolabeled protein meal and/or <40% by 2.0 hours after subject has ingested a radiolabeled protein meal, but (b) >90% emptying by 4 hours after subject has ingested a radiolabeled protein meal.

In embodiments of the systems or methods, the alert sent to the user indicates that the subject has delayed solid gastric emptying.

In embodiments of the systems or methods, a subject is indicated as having a dyspeptic disorder, or as having a condition associated with a dyspeptic disorder, when (1) the solid gastric emptying rate is <30% emptying by 0.5 hours after subject has ingested a radiolabeled protein meal and <70% emptying by 1.0 hours after subject has ingested a radiolabeled protein meal and >90% emptying by 4 hours after subject has ingested a radiolabeled protein meal, but and (2) the glucometric data show (a) a blood glycemic excursion of a predetermined amount or more above a control value or (b) a blood glycemic excursion of a predetermined amount or more below a control value.

In embodiments of the systems or methods, the alert sent to the user indicates that the subject has normal solid gastric emptying but has an elevated or a diminished glycemic excursion.

In embodiments of the systems or methods, a blood glycemic excursion amount in excess of 75 mg/dL above a baseline glucose level at 30 minutes indicates an elevated blood glycemic excursion.

In embodiments of the systems or methods, a blood glycemic excursion amount of 85 mg/dL above a baseline glucose level at 60 minutes indicates an elevated blood glycemic excursion.

In embodiments of the systems or methods, a blood glycemic excursion amount in excess of 30 mg/dL above a baseline glucose level but less than 75 mg/dL above a baseline glucose level at 30 minutes from ingestion of meal indicates a normal blood glycemic excursion.

In embodiments of the system, a blood glycemic excursion amount in excess of 30 mg/dL above a baseline glucose level but less than 80 mg/dL above a baseline glucose level at 60 minutes from ingestion of meal indicates a normal blood glycemic excursion.

In embodiments of the systems or methods, a blood glycemic excursion amount of less than 30 mg/dL above a baseline glucose level at 30 minutes from ingestion of meal indicates a diminished blood glycemic excursion.

In embodiments of the systems or methods, the baseline glucose level is a fasting baseline level of blood glucose of the subject.

In embodiments of the systems or methods, the scintigraphic data comprises a plurality of scintigraphic datum of the subject's gastric emptying rate each obtained at a different time point subsequent to time point zero, wherein time point zero is at the ingestion of the meal.

In embodiments of the systems or methods, a plurality of glucometric data points of the subject's blood glucose level are obtained.

In embodiments of the systems or methods, each glucometric data point of the plurality is obtained simultaneously with, or within 60 seconds of, each of a corresponding scintigraphic datum obtained at different time points subsequent to time point zero.

In embodiments of the systems or methods, the system is used for diagnosing a subject as having a vagal neuropathy gastroparesis, wherein the alert indicates the subject has a diminished glycemic excursion and a delayed solid gastric emptying.

In embodiments of the systems or methods, the system is used for diagnosing a subject as having malabsorption of carbohydrate, wherein the alert indicates the subject has a diminished glycemic excursion and a rapid gastric solid emptying.

In embodiments of the system, the system is used for diagnosing a non-diabetic subject as at increased risk of developing diabetes compared to a standard non-diabetic subject not at risk, wherein the alert indicates the subject has a rapid gastric solid emptying and elevated glycemic excursion.

In embodiments of the systems or methods, the system is used for diagnosing a subject having a dyspepsia as having a functional dyspepsia which should not be treated with a pro-motility therapeutic, wherein the alert indicates the subject has a delayed gastric solid emptying and elevated glycemic excursion.

In embodiments of the systems or methods, the system visibly displays a plot of gastric emptying rates and a plot of postprandial blood glucose levels.

In embodiments of the systems or methods, the system comprises a sliding scale to adjust to a normalized value for gastric emptying rate when the subject ingests an incomplete meal and/or a sliding scale to adjust to a normalized value for postprandial blood glucose level based on the subject's normal starting blood glucose level.

In embodiments of the systems or methods, the scintigraphic for gastric emptying rate for a region if interest is automatically inserted into a plot for visible display to the user.

In embodiments of the systems or methods, a subject is indicated as having a dyspeptic disorder, or as having a condition associated with a dyspeptic disorder, when the dyspeptic disorder comprises: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; or (ix) delayed gastric solid emptying at 2 hours postprandial and delayed blood glycemic excursion. In embodiments of the system, the one of twelve different classifications is one of (i) through (ix) or is: (x) normal gastric solid emptying and elevated blood glycemic excursion; (xi) normal gastric solid emptying and normal blood glycemic excursion; or (xii) normal gastric solid emptying and delayed blood glycemic excursion.

In embodiments of the systems or methods, the subject is diabetic. In embodiments of the system, the subject is not diabetic. In embodiments of the system, the subject is pre-diabetic.

In embodiments of the systems or methods, c) comprises plotting, on a visual display, (i) the measurement of solid gastric emptying rate compared to at least two different first control values for solid gastric emptying in a standard subject and (ii) the carbohydrate gastric emptying rate compared to at least two different second control values for carbohydrate gastric emptying in a standard subject; and wherein d) comprises sending an alert to a user of the system indicating the subject as having a dyspeptic disorder, or as having a condition associated with a dyspeptic disorder, when the solid gastric emptying rate and/or carbohydrate gastric emptying in the subject varies from any of the corresponding control values by a predetermined amount.

In embodiments of the systems or methods, when the measurement of solid gastric emptying rate is compared to at least two different first control values, one of the first control values is a minimum normal solid gastric emptying rate for a standard subject and the other first control value is a maximum normal solid gastric emptying rate for a standard subject.

In embodiments of the systems or methods, when the measurement of carbohydrate gastric emptying is compared to at least two different second control values, one of the second control values is a minimum normal carbohydrate gastric emptying rate for a standard subject and the other second control value is a maximum normal carbohydrate gastric emptying rate for a standard subject.

In embodiments of the systems or methods, the system further comprises a display of subject's orally-communicated gastric symptoms contemporaneously aligned with solid gastric emptying rate and carbohydrate gastric emptying rate in the subject.

In embodiments of the systems or methods, the scintigraphic data is obtained and calculated as a geometric mean of anterior and posterior imaging.

In embodiments of the systems or methods, the scintigraphic data is obtained is corrected for radioisotope decay.

Also provided herein, in embodiments, is a system for diagnosing a subject as having a dyspeptic disorder, or as having a condition associated with a dyspeptic disorder, or for classifying gastric emptying in a subject as one of twelve different classifications, comprising: a) obtaining, from a subject that has ingested at a set time point a meal comprising a radiolabeled carbohydrate and radiolabeled protein, a first scintigraphic data set of the subject's gastric carbohydrate emptying rate and a second scintigraphic data set of gastric protein emptying rate at a plurality of time points subsequent to the set time point; b) integrating, using a processor, the first and second scintigraphic data sets to provide, respectively, a measurement of gastric carbohydrate emptying rate and a measurement of gastric protein emptying rate and in the subject; c) listing and/or plotting on a visual display the measurement of gastric protein emptying rate and gastric carbohydrate emptying rate compared to at least a first control value for gastric protein emptying rate and compared to at least a second control value for gastric carbohydrate emptying in a standard subject; d) sending an alert to a user of the system indicating the subject as having a dyspeptic disorder, or as having a condition associated with a dyspeptic disorder, when the gastric protein emptying rate and/or gastric carbohydrate emptying rate in the subject varies from the corresponding control value by a predetermined amount.

In embodiments of the systems or methods, the alert is unique for each of one of nine different categories of dyspeptic disorder, or of the condition associated with a dyspeptic disorder.

In embodiments of the systems or methods, the radiolabeled carbohydrate is radiolabeled with $^{113m}$Indium or $^{67}$Ga and/or the radiolabeled protein comprises $^{99m}$Tc-sulfur colloid or other radiolabeled colloids of $^{99m}$Tc. In embodiments, the carbohydrate is in liquid form and is radiolabeled directly or without attachment via a colloid. In embodiments of the systems or methods, the scintigraphic data comprises mean geometric amount of $^{99m}$Tc-sulfur colloid movement quantified from a user-determined region of interest the subject. In embodiments of the systems or methods, the scintigraphic data comprises mean geometric amount of $^{113m}$Indium or $^{67}$Ga radiocolloids quantified from a user-determined region of interest the subject.

In embodiments of the systems or methods, a baseline amount of radiolabel activity in a user-determined region of interest of the subject is determined at, or immediately after, ingestion of the meal and is obtained as scintigraphic data using a gamma camera.

In embodiments of the systems or methods, (i) the first control value and/or second control value are normalized for total kilocalorie amount of meal ingested by subject, and/or (ii) the second control value is normalized for subject's fasting glucose level.

In embodiments of the systems or methods, a subject is indicated as having a dyspeptic disorder, or as having a condition associated with a dyspeptic disorder, when the solid gastric emptying rate is >30% emptying by 0.5 hours after subject has ingested a meal comprising a radiolabeled carbohydrate and radiolabeled protein and/or >70% emptying by 1.0 hours after subject has ingested a meal comprising a radiolabeled carbohydrate and radiolabeled protein.

In embodiments of the systems or methods, the alert sent to the user indicates that the subject has rapid gastric solid emptying.

In embodiments of the systems or methods, a subject is indicated as having a dyspeptic disorder, or as having a condition associated with a dyspeptic disorder, when the solid gastric emptying rate is (i)<90% emptying by 4 hours after subject has ingested a meal comprising a radiolabeled carbohydrate and radiolabeled protein or (ii) (a)<10% emptying by 1.0 hours after subject has ingested a meal comprising a radiolabeled carbohydrate and radiolabeled protein and/or <40% by 2.0 hours after subject has ingested a meal comprising a radiolabeled carbohydrate and radiolabeled protein, but (b) >90% emptying by 4 hours after subject has ingested a meal comprising a radiolabeled carbohydrate and radiolabeled protein.

In embodiments of the systems or methods, the alert sent to the user indicates that the subject has delayed solid gastric emptying.

In embodiments of the systems or methods, a subject is indicated as having a dyspeptic disorder, or as having a condition associated with a dyspeptic disorder, when (1) the solid gastric emptying rate is <30% emptying by 0.5 hours after subject has ingested a meal comprising a radiolabeled carbohydrate and radiolabeled protein and <70% emptying by 1.0 hours after subject has ingested a meal comprising a radiolabeled carbohydrate and radiolabeled protein and >90% emptying by 4 hours after subject has ingested a meal comprising a radiolabeled carbohydrate and radiolabeled protein, but and (2) the glucometric data show (a) a blood glycemic excursion of a predetermined amount or more above a control value or (b) a blood glycemic excursion of a predetermined amount or more below a control value.

In embodiments of the systems or methods, the alert sent to the user indicates that the subject has normal solid gastric emptying but has an elevated or a diminished glycemic excursion.

In embodiments of the systems or methods, a blood glycemic excursion amount in excess of 75 mg/dL above a baseline glucose level at 30 minutes indicates an elevated blood glycemic excursion which is associated with rapid gastric emptying of the carbohydrate meal component.

In embodiments of the systems or methods, a blood glycemic excursion amount of 85 mg/dL above a baseline glucose level at 60 minutes indicates an elevated blood glycemic excursion which is associated with rapid gastric emptying of the carbohydrate meal component.

In embodiments of the systems or methods, a blood glycemic excursion amount in excess of 30 mg/dL above a baseline glucose level but less than 75 mg/dL above a baseline glucose level at 30 minutes from ingestion of meal indicates a normal blood glycemic excursion which is associated with normal gastric emptying of the carbohydrate meal component.

In embodiments of the systems or methods, a blood glycemic excursion amount in excess of 30 mg/dL above a baseline glucose level but less than 80 mg/dL above a baseline glucose level at 60 minutes from ingestion of meal indicates a normal blood glycemic excursion.

In embodiments of the systems or methods, a blood glycemic excursion amount of less than 30 mg/dL above a baseline glucose level at 30 minutes from ingestion of meal indicates a diminished blood glycemic excursion which is associated with delayed gastric emptying of the carbohydrate meal component.

In embodiments of the systems or methods, the baseline glucose level is a fasting baseline level of blood glucose of the subject.

In embodiments of the systems or methods, the scintigraphic data comprises a plurality of scintigraphic datum of the subject's gastric emptying rate each obtained at a different time point subsequent to time point zero, wherein time point zero is at the ingestion of the meal.

In embodiments of the systems or methods, a plurality of glucometric data points of the subject's blood glucose level are obtained.

In embodiments of the systems or methods, each glucometric data point of the plurality is obtained simultaneously with, or within 60 seconds of, each of a corresponding scintigraphic datum obtained at different time points subsequent to time point zero.

In embodiments of the systems or methods, the system is used for diagnosing a subject as having a vagal neuropathy gastroparesis, wherein the alert indicates the subject has a diminished glycemic excursion and a delayed solid gastric emptying.

In embodiments of the systems or methods, the system is used for diagnosing a subject as having malabsorption of carbohydrate, wherein the alert indicates the subject has a diminished glycemic excursion and a rapid gastric solid emptying.

In embodiments of the systems or methods, the system is used for diagnosing a non-diabetic subject as at increased risk of developing diabetes compared to a standard non-diabetic subject not at risk, wherein the alert indicates the subject has a rapid gastric solid emptying and elevated glycemic excursion.

In embodiments of the systems or methods, the system is used for diagnosing a subject having a dyspepsia as having a functional dyspepsia which should not be treated with a pro-motility therapeutic, wherein the alert indicates the subject has a delayed gastric solid emptying and elevated glycemic excursion.

In embodiments of the systems or methods, the system visibly displays a plot of protein gastric emptying rates and a plot of carbohydrate gastric emptying rates.

In embodiments of the systems or methods, the system comprises a sliding scale to adjust to a normalized value for gastric emptying rates when the subject ingests an incomplete meal.

In embodiments of the systems or methods, the scintigraphic for gastric emptying rate for a region if interest is automatically inserted into a plot for visible display to the user.

In embodiments of the systems described herein, a subject is indicated as having a dyspeptic disorder, or as having a condition associated with a dyspeptic disorder, when the dyspeptic disorder comprises: (i) rapid gastric protein emptying and elevated gastric carbohydrate emptying; (ii) rapid gastric protein emptying and normal gastric carbohydrate emptying; (iii) rapid gastric protein emptying and delayed gastric carbohydrate emptying; (iv) delayed gastric protein emptying at 4 hours postprandial and elevated gastric carbohydrate emptying; (v) delayed gastric protein emptying at 2 hours postprandial and normal gastric carbohydrate emptying; (vi) delayed gastric protein emptying at 2 hours postprandial and delayed gastric carbohydrate emptying; (vii) delayed gastric protein emptying at 2 hours postprandial and elevated gastric carbohydrate emptying; (viii) delayed gastric protein emptying at 2 hours postprandial and normal gastric carbohydrate emptying; or (ix) delayed gastric protein emptying at 2 hours postprandial and delayed gastric carbohydrate emptying. In embodiments of the system, the one of twelve different classifications is one of (i) through (ix) or is: (x) normal gastric protein emptying and elevated gastric carbohydrate emptying; (xi) normal gastric protein emptying and normal gastric carbohydrate emptying; or (xii) normal gastric protein emptying and delayed gastric carbohydrate emptying.

In embodiments of the systems or methods, the subject is diabetic. In embodiments of the systems or methods, the subject is not diabetic. In embodiments of the systems or methods, the subject is pre-diabetic.

In embodiments of the systems or methods, c) comprises plotting, on a visual display, (i) the measurement of gastric protein emptying rate compared to at least two different first control values for gastric protein emptying rate in a standard subject and (ii) the carbohydrate gastric emptying rate compared to at least two different second control values for gastric carbohydrate emptying in a standard subject; and wherein d) comprises sending an alert to a user of the system indicating the subject as having a dyspeptic disorder, or as having a condition associated with a dyspeptic disorder, when the gastric protein emptying rate and/or gastric carbohydrate emptying in the subject varies from any of the corresponding control values by a predetermined amount.

In embodiments of the systems or methods, when the measurement of gastric protein emptying rate is compared to at least two different first control values, one of the first control values is a minimum normal gastric protein emptying rate for a standard subject and the other first control value is a maximum normal gastric protein emptying rate for a standard subject.

In embodiments of the systems or methods, when the measurement of gastric carbohydrate emptying is compared to at least two different second control values, one of the second control values is a minimum normal gastric carbohydrate emptying rate for a standard subject and the other second control value is a maximum normal gastric carbohydrate emptying rate for a standard subject.

In embodiments of the systems or methods, the system further comprises a display of subject's orally-communicated gastric symptoms contemporaneously aligned with gastric protein emptying rate and gastric carbohydrate emptying rate in the subject.

In embodiments of the systems or methods, the scintigraphic data is obtained and calculated as a geometric mean of anterior and posterior imaging.

In embodiments of the systems or methods, the scintigraphic data is obtained is corrected for radioisotope decay.

In embodiments the systems or method further comprises displaying the alert visually and/or audibly on the GUI.

In embodiments, provided is a system for classifying gastric emptying in a subject, comprising: a) a first scintigraphic measurement equipment configured to measure, from a subject that has ingested at a set time point a meal comprising carbohydrate and radiolabeled protein, first scintigraphic data of the subject's protein solid gastric emptying rate at a plurality of time points over a predetermined amount of time, subsequent to the set time point; b) a second scintigraphic measurement equipment configured to measure, from the subject, second scintigraphic data of carbohydrate gastric emptying at the plurality of time points subsequent to the set time point; c) a computer system, comprising at least one processor and computer readable memory operatively connected to the at least one processor, which computer system is operatively connected to the first scintigraphic measurement equipment and the second scintigraphic measurement equipment, and wherein the computer system is configured to perform the steps of: (1) storing on the memory a plurality of control values in one or more databases, wherein plurality of control values comprise: (A) a first set of protein solid gastric emptying control values, wherein each protein solid gastric emptying control value of the first set of protein solid gastric emptying control values corresponds to one time point of the plurality of time points, and wherein for a first set of time points of the plurality of time points, the first set of protein solid gastric emptying control values comprises at least one of (1) a predetermined upper protein solid gastric emptying value and (2) a predetermined lower protein solid gastric emptying value; and (B) a second set of carbohydrate gastric emptying control values, wherein each carbohydrate gastric emptying control value of the second set of carbohydrate gastric emptying control values corresponds to one time point of the plurality of time points, and wherein for a second set of time points of the plurality of time points, the second set of carbohydrate gastric emptying control values corresponds to at least one of (1) a predetermined upper carbohydrate gastric emptying level value, and (2) a predetermined lower carbohydrate gastric emptying level value; (2) at each of the plurality of time points, performing the following steps: (i) obtaining, from the first scintigraphic measurement equipment, at a respective time point respective first scintigraphic data for the subject, and storing said respective time point and said respective first scintigraphic data in memory; (ii) obtaining, from the second scintigraphic measurement equipment, at the respective time point respective second scintigraphic data for the subject, and storing said respective time point and said respective second scintigraphic data in memory; (iii) accessing, using the processor from memory, for at least the respective time point, at least the following respective time point information: a. respective first scintigraphic data; b. respective predetermined upper protein solid gastric emptying value to the extent available; c. respective predetermined lower protein solid gastric emptying value to the extent available; d. respective second scintigraphic data; e. respective predetermined upper carbohydrate gastric emptying value to the extent available; f. respective predetermined lower carbohydrate gastric emptying value to the extent available; (iv) generating, by the computer system, first machine-readable instructions to render a first graphical user interface including a first graphical representation of: a. the first scintigraphic data for the subject at the respective time point; b. the predetermined upper protein solid gastric emptying value at the respective time point, to the extent available; and c. the predetermined lower protein solid gastric emptying value at the respective time point, to the extent available; and (v) generating, by the computing system, second machine-readable instructions to render a second graphical user interface including a second graphical representation of: a. the second scintigraphic data for the subject at the respective time point; b. the predetermined upper carbohydrate gastric emptying value, at the respective time point, to the extent available; and c. the predetermined lower carbohydrate gastric emptying value at the respective time point, to the extent available; d) transmitting, by the computer system to a first electronic device, the first machine-readable instructions so as to cause the first electronic device to render a graphical user interface on a first screen of a display associated with the first electronic device comprising a visual display of the subject's protein solid gastric emptying rate; e) transmitting by the computer system to the first electronic device, the second machine-readable instructions so as to cause the first electronic device to render a graphical user interface on a second screen of the display associated with the first electronic device comprising a visual display of the subject's carbohydrate gastric emptying rate; f) monitoring, by the at least one processor of the computer system, the subject's protein solid gastric emptying rate and of the subject's blood glucose level rate to determine at least one event of a plurality of events has occurred, wherein the plurality of events includes: (i) rapid gastric solid emptying and rapid carbohydrate gastric emptying; (ii) rapid gastric solid emptying and normal carbohydrate gastric emptying; (iii) rapid gastric solid emptying and delayed carbohydrate gastric emptying; (iv) delayed gastric solid emptying at 4 hours postprandial and delayed carbohydrate gastric emptying; (v) delayed gastric solid emptying at 2 hours postprandial and normal carbohydrate gastric emptying; (vi) delayed gastric solid emptying at 2 hours postprandial and delayed carbohydrate gastric emptying; (vii) delayed gastric solid emptying at 2 hours postprandial and rapid carbohydrate gastric emptying; (viii) delayed gastric solid emptying at 2 hours postprandial and normal carbohydrate gastric emptying; (ix) delayed gastric solid emptying at 2 hours postprandial and delayed carbohydrate gastric emptying; (x) normal gastric solid emptying and rapid carbohydrate gastric emptying; (xi) normal gastric solid emptying and delayed carbohydrate gastric emptying; and (xii) normal gastric solid emptying and normal carbohydrate gastric emptying; g) transmitting, from the computer system to the first electronic device or a second electronic device, in response to the at least one processor of the computer system determining the at least one event of the plurality of events has occurred, an alert wherein the alert indicates that the subject has a dyspeptic disorder, or as having a condition associated with a dyspeptic disorder, if the at least one event is one or more of f)(i) through f)(xi), and wherein the alert indicates that the subject does not have a dyspeptic disorder or a condition associated with a dyspeptic disorder if the at least one event is f)(xii).

Also provided is a method of treating a subject for a condition associated with a gastric emptying disorder comprising determining which gastric emptying disorder the subject has using a system described herein and administering to the subject a medication for that gastric emptying disorder.

In embodiments, the subject is determined to have a gastric emptying disorder which is a functional dyspepsia that should not be treated with a pro-motility therapeutic and wherein the medication administered comprises pramlintide or a GLP-1 agonist. In embodiments, the medication administered comprises pramlintide. In embodiments, the medication administered comprises a GLP-1 agonist.

In embodiments, the subject is determined to have a gastric emptying disorder which is a functional dyspepsia that should not be treated with a pro-motility therapeutic and wherein the medication administered comprises a soluble fiber.

In embodiments, the subject is determined to have a gastric emptying disorder which comprises an elevated blood glycemic excursion, and wherein the medication administered comprises pramlintide, metformin, or an oral protease inhibitor.

In embodiments, the subject is determined to have a gastric emptying disorder which comprises an elevated blood glycemic excursion, and wherein the medication administered comprises a treatment which attenuates development of diabetes, hypertension, obesity or metabolic syndrome.

In embodiments, the subject is determined to have a gastric emptying disorder which is a functional dyspepsia that should be treated with a pro-motility therapeutic and wherein the medication administered comprises a pro-motility therapeutic.

In embodiments, the pro-motility therapeutic is a cholinergic agonist, prokinetic agent, or opioid antagonist. In embodiments, the pro-motility therapeutic is a cholinergic agonist. In embodiments, the pro-motility therapeutic is a prokinetic agent. In embodiments, the pro-motility therapeutic is an opioid antagonist.

Also provided is a method of prophylactically treating a subject against a condition associated with a gastric emptying disorder comprising determining which gastric emptying disorder the subject has using the system described herein and administering to the subject a prophylactic medication for delaying or reducing development of the condition.

In embodiments, the condition is diabetes or pre-diabetes and the subject is administered pramlintide, metformin, or an oral protease inhibitor.

In embodiments, the subject is determined to have a gastric emptying disorder which comprises an elevated blood glycemic excursion.

Also provided is a method of diagnosing a subject as having a dyspeptic disorder, or as having a condition associated with a dyspeptic disorder, or for classifying gastric emptying in a subject as one of twelve different classifications, comprising quantitatively determining, simultaneously, a carbohydrate gastric emptying rate and a protein gastric emptying rate of the subject and plotting on a visual display a measurement of protein gastric emptying rate compared to at least two different first control values and a carbohydrate gastric emptying rate compared to at least two different second control values wherein the control values are set from a standard subject;
receiving an alert as a user of the system indicating the subject as having a dyspeptic disorder, or as having a condition associated with a dyspeptic disorder, when the solid gastric emptying rate and/or carbohydrate gastric emptying in the subject varies from any of the corresponding control values by a predetermined amount, and thereby diagnosing a subject as having a dyspeptic disorder, or as having a condition associated with a dyspeptic disorder, or for classifying gastric emptying in a subject as one of twelve different classifications.

In embodiments, the dyspeptic disorder comprises: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; or (ix) delayed gastric solid emptying at 2 hours postprandial and delayed blood glycemic excursion. In embodiments, the one of twelve different classifications is one of (i) through (ix) or is: (x) normal gastric solid emptying and elevated blood glycemic excursion; (xi) normal gastric solid emptying and normal blood glycemic excursion; or (xii) normal gastric solid emptying and delayed blood glycemic excursion.

In embodiments, the quantitative determining of the gastric emptying rates is effected using a system as described herein.

In embodiments, also provided is a method of obtaining differentiation of protein and carbohydrate gastric emptying rates in a subject, comprising quantitatively determining a carbohydrate gastric emptying rate and a protein gastric emptying rate of the subject and plotting on a visual display a measurement of protein gastric emptying rate compared to at least two different first control values and a carbohydrate gastric emptying rate compared to at least two different second control values wherein the control values are set from a standard subject; classifying gastric emptying in a subject as one of twelve different classifications from the following: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; (ix) delayed gastric solid emptying at 2 hours postprandial and delayed blood glycemic excursion; (x) normal gastric solid emptying and elevated blood glycemic excursion; (xi) normal gastric solid emptying and normal blood glycemic excursion; or (xii) normal gastric solid emptying and delayed blood glycemic excursion, so as to thereby obtain differentiation of protein and carbohydrate gastric emptying rates in a subject.

In embodiments, the quantitative determining of the gastric emptying rates is effected using a system as described herein.

In embodiments, the quantitative determining of the gastric emptying rates is effected in under 4 hours. In embodiments, the quantitative determining of the gastric emptying rates is effected in under 3 hours. In embodiments, the quantitative determining of the gastric emptying rates is effected in under 2 hours. In embodiments, the quantitative determining of the gastric emptying rates is effected in under 1 hour.

In embodiments of the methods described herein, the subject is diabetic. In embodiments of the methods described herein, the subject is not diabetic. In embodiments of the system, the subject is pre-diabetic.

In embodiments of the method a separate blood glucose measurement is not made within 1 hour prior to initiating the method. In embodiments of the method a separate blood glucose measurement is not made immediately prior to initiating the method.

In embodiments a meal as described herein comprises or consists of:

0.5-1.0 mCi (18.5-37 mSv) $^{99m}$Tc-SC scrambled with 120 gm liquid egg white plus two slices of white toast, 30 gm strawberry jelly, and 120 ml water.

In embodiments where a therapeutic or prophylactic treatment is administered, administration can be intravenously, parenterally, auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, and/or uretheral, to name a few.

As used herein, a control amount or value is a value decided or obtained, usually beforehand (predetermined), as a normal or standard value. The concept of a control is well-established in the field, and can be determined, in a non-limiting example, empirically from standard or non-afflicted subjects (versus afflicted subjects, including afflicted subjects having different grades of the relevant gastric emptying classifications) on an individual or population basis, and/or may be normalized as desired (in non-limiting examples, for volume, mass, age, location, gender) to negate the effect of one or more variables.

In embodiments, a standard subject is a human without a dyspeptic disorder. In embodiments, a standard subject is a human without a condition associated with a dyspeptic disorder.

In embodiments of the systems or methods, embodiments of the invention optionally comprises calculating, by the at least one processor of the computer system, a first control range, wherein the first control range represents an upper solid gastric emptying control rate and a lower solid gastric emptying control rate, wherein calculating the first control range comprises: calculating, by the at least one processor of the computer system, the upper solid gastric emptying control rate at the plurality of time points, wherein calculating the upper solid gastric emptying control rate is based on at least the first set of solid gastric emptying control values and the predetermined amount of time; calculating, by the at least one processor of the computer system, the lower solid gastric emptying control rate at the plurality of time points, wherein calculating the lower solid gastric emptying control rate is based on at least the first set of solid gastric emptying control values and the predetermined amount of time; calculating, by the at least one processor of a computer system, a second control range, wherein the second control range represents an upper carbohydrate gastric emptying control rate and a lower carbohydrate gastric emptying control rate, wherein calculating the second control range comprises: calculating, by the at least one processor of the computer system, the upper carbohydrate gastric emptying control rate at the plurality of time points, wherein calculating the upper carbohydrate gastric emptying control rate is based on at least the second set of carbohydrate gastric emptying control values and the predetermined amount of time; and calculating, by the at least one processor of the computer system, the lower carbohydrate gastric emptying control rate at the plurality of time points, wherein calculating the lower carbohydrate gastric emptying control rate is based on at least the second set of carbohydrate gastric emptying control values and the predetermined amount of time.

Figure 12A:
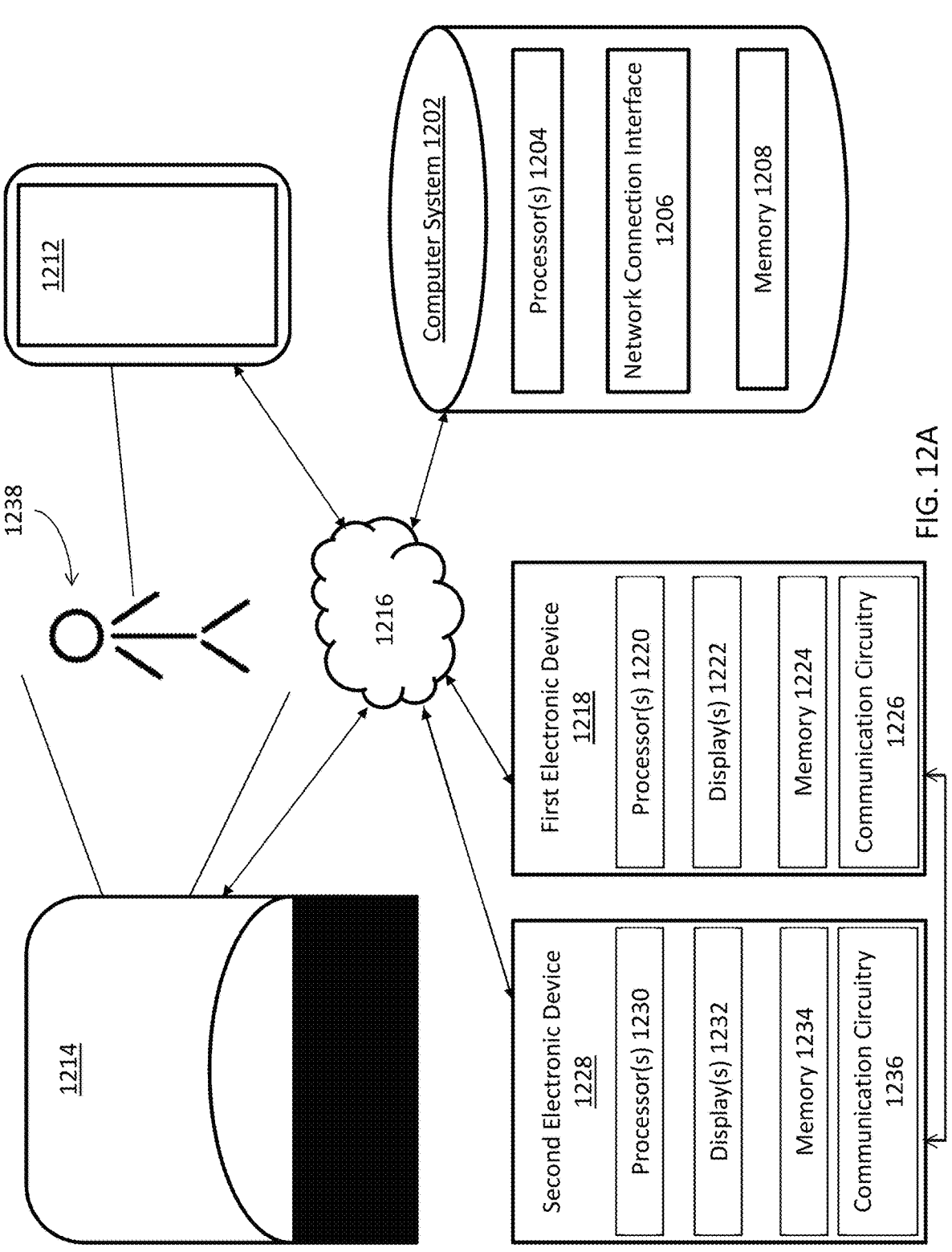
FIG. 12A: An exemplary block diagram illustrating a system for classifying gastric emptying in a subject 1238, which, may be used for diagnosing whether the subject 1238 as has a dyspeptic disorder or a condition associated with a dyspeptic disorder with either abnormally delayed or abnormally rapid gastric emptying of the solid protein or the carbohydrate meal components.

FIG. 12A is an exemplary block diagram illustrating a system for classifying gastric emptying in a subject 1238, which, may be used for diagnosing whether the subject 1238 as has a dyspeptic disorder or a condition associated with a dyspeptic disorder. Referring to FIG. 12A, an exemplary computer system 1202 in communication with exemplary scintigraphic measurement equipment 1214, exemplary glucometric measurement equipment 1212, an exemplary first electronic device 1218 and/or an exemplary second electronic device 1228 via network 1216. The network 1216 may be the Internet, an intranet network, a local area network, other wireless or other hardwired connection or connections, or a combination of one or more thereof, by which individual components of the system may communicate. In embodiments, the computer system 1202, the scintigraphic measurement equipment 1214, the glucometric measurement equipment 1212, the first electronic device 1218 and/or the second electronic device 1228 may include personal computers and/or mobile devices, such as cellphones, smartwatches, other smart wearable devices, exercise equipment with user interfaces, and the like, with Internet access that are uniquely identifiable by Internet Protocol (IP) addresses, Internet cookies, Media Access Control (MAC) identifiers, or online personal accounts of the individual users, corporations, and/or organizations associated with the computer system 1202, the scintigraphic measurement equipment 1214, the glucometric measurement equipment 1212, the first electronic device 1218 and/or the second electronic device 1228, either directly or through another electronic device.

Communications systems for facilitating network 1216 can include hardware (e.g., hardware for wired and/or wireless connections) and/or software. In embodiments, communications systems can include one or more communications chipsets, such as a GSM chipset, CDMA chipset, LTE chipset, Wi-Fi chipset, Bluetooth chipset, to name a few, and/or combinations thereof. Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Wired connections may be provided through telephone ports, Ethernet ports, USB ports, and/or other data ports, such as Apple 30-pin connector ports or Apple Lightning connector ports, to name a few. Wireless connections may include cellular or cellular data connections and protocols (e.g., digital cellular, PCS, CDPD, GPRS, EDGE, CDMA2000, 1×RTT, RFC 1149, Ev-DO, HSPA, UMTS, 3G, 4G, and/or LTE, to name a few), Bluetooth, Bluetooth Low Energy, Wi-Fi, radio, satellite, infrared connections, ZigBee communication protocols, to name a few. Communications interface hardware and/or software, which may be used to communicate over wired and/or wireless connections, may include Ethernet interfaces (e.g., supporting a TCP/IP stack), X.25 interfaces, T1 interfaces, and/or antennas, to name a few. Computer systems may communicate with other computer systems or devices directly and/or indirectly, e.g., through a data network 1216, such as the Internet, a telephone network, a mobile broadband network (such as a cellular data network), a mesh network, Wi-Fi, WAP, LAN, and/or WAN, to name a few.

The glucometric measurement equipment 1212, may be one or more electronic devices that are configured to measure the blood glucose level of a subject at one point in time or over a period of time. In embodiments, the glucometric measurement equipment 1212 may measure the blood glucose level of the subject 1238. This process is described in more detail below in connection with FIGS. 12B-C and 13A-C. In embodiments, the glucometric measurement equipment 1212 is medical equipment for determining the approximate concentration of glucose in the blood of a subject (e.g., subject 1238). The glucometric measurement equipment 1212 can also be a strip of glucose paper dipped into a substance and measured to a glucose chart and/or a glucometer, to name a few. In embodiments, the glucometric measurement equipment 1212 may display the level the blood glucose level of a subject in units of mg/dl or mmol/l. In embodiments, the glucometric measurement equipment 1212 may include one or more processor(s), one or more display(s), memory, and communications circuitry, which, in embodiments, may be similar to processor(s) 1220, display(s) 1222, memory 1224, and communication circuitry 1226, respectively, the descriptions of which applying herein.

The scintigraphic measurement equipment 1214, in embodiments, may be one or more electronic devices that are configured to measure the solid gastric emptying rate at one point in time or over a period of time. In embodiments, the scintigraphic measurement equipment 1214 may be a gamma camera. In embodiments, the scintigraphic measurement equipment 1214 may measure the solid gastric emptying rate of the subject 1238. This process is described in more detail below in connection with FIGS. 12B-C and 13A-C. In embodiments, the scintigraphic measurement equipment 1214 may include one or more processor(s), one or more display(s), memory, and communications circuitry, which, in embodiments, may be similar to processor(s) 1220, display(s) 1222, memory 1224, and communication circuitry 1226, respectively, the descriptions of which applying herein.

The first electronic device 1218 and/or the second electronic device 1228, as used herein, may, in embodiments, correspond to any suitable type of electronic device including, but are not limited to, desktop computers, mobile computers (e.g., laptops, ultrabooks), mobile phones, smart phones, tablets, televisions, set top boxes, smart televisions, personal display devices, large scale display devices (e.g., billboards, street signs, etc.), personal digital assistants ("PDAs"), gaming consoles and/or devices, virtual reality devices smart furniture, smart household devices (e.g., refrigerators, microwaves, etc.), smart vehicles (e.g., cars, trucks, motorcycles, etc.), smart transportation devices (e.g., boats, ships, trains, airplanes, etc.), wearable devices (e.g., watches, pins/broaches, headphones, etc.), smart security systems, and/or smart accessories (e.g., light bulbs, light switches, electrical switches, etc.), to name a few. In some embodiments, personal user device 10-1 and/or optional second personal user device 10-1A may be relatively simple or basic in structure such that no, or a minimal number of, mechanical input option(s) (e.g., keyboard, mouse, track pad) or touch input(s) (e.g., touch screen, buttons) are included. For example, the first electronic device 1218 and/or the second electronic device 1228 may be able to receive and output audio, and may include power, processing capabilities, storage/memory capabilities, and communication capabilities. However, in other embodiments, the first electronic device 1218 and/or the second electronic device 1228 may include one or more components for receiving mechanical inputs or touch inputs, such as a touch screen and/or one or more buttons.

The first electronic device 1218 and/or the second electronic device 1228 may, in embodiments, be a voice activated electronic device. A voice activated electronic device, as described herein, may correspond to any device capable of being activated in response to detection of a specific word (e.g., a word, a phoneme, a phrase or grouping of words, or any other type of sound, or any series of temporally related sounds). For example, a voice activated electronic device may be one or more of the following: Amazon Echo®; Amazon Echo Show®; Amazon Echo Dot®; Smart Television (e.g., Samsung® Smart TV's); Google Home®; Voice Controlled Thermostats (e.g., Nest®; Honeywell® Wi-Fi Smart Thermostat with Voice Control), smart vehicles, smart transportation devices, wearable devices (e.g., Fitbit®), and/or smart accessories, to name a few.

The first electronic device 1218 and/or the second electronic device 1228 may include one or more processor(s) (processor(s) 1220 and 1230 respectively), one or more display(s) (display(s) 1222 and 1232 respectively), memory (1224 and 1234 respectively), and communication circuitry (1226 and 1236 respectively).

One or more processor(s) (processor(s) 1220 and 1230 respectively), which may be referred to herein collectively as processor(s) 1220, may include any suitable processing circuitry capable of controlling operations and functionality of the first electronic device 1218 and the second electronic device 1228, as well as facilitating communications between various components within the first electronic device 1218 and the second electronic device 1228. In some embodiments, processor(s) 1220 may include a central processing unit ("CPU"), a graphic processing unit ("GPU"), one or more microprocessors, a digital signal processor, or any other type of processor, or any combination thereof. In some embodiments, the functionality of processor(s) 1220 may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 1220 may include its own local memory, which may store program systems, program data, and/or one or more operating systems. However, processor(s) 1220 may run an operating system ("OS") for the first electronic device

1218 and the second electronic device 1228, and/or one or more firmware applications, media applications, and/or applications resident thereon. In some embodiments, processor(s) 1220 may run a local client script for reading and rendering content received from one or more websites. For example, processor(s) 1220 may run a local JavaScript client for rendering HTML or XHTML content received from a particular URL accessed by the first electronic device 1218 and the second electronic device 1228.

In embodiments, as mentioned above, the first electronic device 1218 and the second electronic device 1228 may include display screens (display(s) 1222 and 1232 respectively). Display(s) 1222 and/or 1232, which may be referred to herein collectively as display(s) 1222, may correspond to a display device and/or touch screen, which may be any size and/or shape and may be located at any portion of the first electronic device 1218 and the second electronic device 1228. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Still further, a touch screen may, in some embodiments, correspond to a display device including capacitive sensing panels capable of recognizing touch inputs thereon. For instance, display(s) 1222 may correspond to a projected capacitive touch ("PCT"), screen include one or more row traces and/or driving line traces, as well as one or more column traces and/or sensing lines. In some embodiments, display(s) 1222 may be an optional component for the first electronic device 1218 and the second electronic device 1228. For instance, the first electronic device 1218 and the second electronic device 1228 may not include display(s) 1222. Such devices, sometimes referred to as "headless" devices, may output audio, or may be in communication with a display device for outputting viewable content.

Display(s) 1222, in embodiments, may include an insulator portion, such as glass, coated with a transparent conductor, such as indium tin oxide ("InSnO" or "ITO"). In general, one side of the touch screen display may be coated with a conductive material. A voltage may be applied to the conductive material portion generating a uniform electric field. When a conductive object, such as a human finger, stylus, or any other conductive medium, contacts the non-conductive side, typically an outer surface of display(s) 1222, a capacitance between the object and the conductive material may be formed. Processor(s) 1220 may be capable of determining a location of the touch screen associated with where the capacitance change is detected, and may register a touch input as occurring at that location.

In some embodiments, display(s) 1222 may include multiple layers, such as a top coating layer, a driving line layer, a sensing layer, and a glass substrate layer. As mentioned previously, the glass substrate layer may correspond to an insulator portion, while the top coating layer may be coated with one or more conductive materials. The driving line layer may include a number of driving lines, and the sensing layer may include a number of sensing lines, which are described in greater detail below. One or more additional layers, or spaces between layers, may be included. Furthermore, any suitable number of driving lines and sensing lines for driving the line layer and the sensing layer, respectively, may be used.

In some embodiments, the driving lines and the sensing lines of the driving line layer and the sensing line layer, respectively, may form a number of intersection points, where each intersection functions as its own capacitor. Each sensing line may be coupled to a source, such that a charge is provided to each sensing line, and changes in capacitance of a particular driving line and sensing line are detectable thereby. In response to a conductive object being brought proximate, or substantially touching an outer surface of the top coating layer, a mutual capacitance of a particular capacitor (e.g., an intersection point) may reduce in magnitude. In other words, a voltage drop may be detected at a location on display(s) 1222 corresponding to where a conductive object contacted display(s) 1222.

A change in capacitance may be measured to determine a location on the touch screen where the object has contacted the surface. For example, if an individual touches a point on display(s) 1222, then a corresponding driving line and sensing line that intersect at that point may be identified. A location of the point may have one or more pixels associated with that location, and therefore one or more actions may be registered for an item or items that are displayed at that location. Processor(s) 1220 of the first electronic device 1218 and the second electronic device 1228 may be configured to determine which pixels are associated with a particular location point, and which item or items are also displayed at that pixel location. Furthermore, the first electronic device 1218 and the second electronic device 1228 may be configured to cause one or more additional actions to occur to the item or items being displayed on display(s) 1222 based on a temporal duration the touch input, and or if one or more additional touch inputs are detected. For example, an object that contacted display(s) 1222 at a first location may be determined, at a later point in time, to contact display(s) 1222 at a second location. In the illustrative example, an object may have initially contacted display(s) 1222 at the first location and moved along a particular driving line to the second location. In this scenario, a same driving line may have detected a change in capacitance between the two locations, corresponding to two separate sensing lines.

The number of driving lines and sensing lines, and therefore the number of intersection points, may directly correlate to a "resolution" of a touch screen. For instance, the greater the number of intersection points (e.g., a greater number of driving lines and sensing lines), the greater precision of the touch input. For instance, a touch screen display(s) 1222 having 100 driving lines and 100 sensing lines may have 100 intersection points, and therefore 100 individual capacitors, while a touch screen display(s) 1222 having 10 driving lines and 10 sensing lines may only have 10 intersection points, and therefore 10 individual capacitors. Therefore, a resolution of the touch screen having 100 intersection points may be greater than a resolution of the touch screen having 10 intersection points. In other words, the touch screen having 100 intersection points may be able to resolve a location of an object touching the touch screen with greater precision than the touch screen having 10 intersection points. However, because the driving lines and sensing lines require a voltage to be applied to them, this may also mean that there is a larger amount of power drawn by the first electronic device 1218 and the second electronic device 1228, and therefore the fewer driving lines and/or sensing lines used, the smaller the amount of power that is needed to operate the touch screen display.

In some embodiments, display(s) 1222 may correspond to a high-definition ("HD") display. For example, display(s) 1222 may display images and/or videos of 720p, 1080p, 1080i, or any other image resolution. In these particular scenarios, display(s) 1222 may include a pixel array configured to display images of one or more resolutions. For instance, a 720p display may present a 1024 by 768, 1280 by 720, or 1366 by 768 image having 786,432; 921,600; or 1,049,088 pixels, respectively. Furthermore, a 1080p or 1080i display may present a 1920 pixel by 1080 pixel image having 2,073,600 pixels. However, the aforementioned display ratios and pixel numbers are merely exemplary, and any suitable display resolution or pixel number may be employed for display(s) 1222, such as non-HD displays, 4K displays, and/or ultra displays.

In embodiments, display(s) 1222 may include multiple screens that may be configured to display multiple graphical user interfaces. For example, display(s) 1222 may be configured to display a first graphical user interface representing data retrieved by the scintigraphic measurement equipment 1214 while simultaneously displaying a second graphical user interface representing data retrieved by the glucometric measurement equipment 1212.

As mentioned above, the first electronic device 1218 and the second electronic device 1228 may include memory (memory 1224 and 1234 respectively). Memory 1224 and 1234, which may be referred to herein collectively as memory 1224, may include one or more types of storage mediums such as any volatile or non-volatile memory, or any removable or non-removable memory implemented in any suitable manner to store data for the first electronic device 1218 and the second electronic device 1228. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 706 may be implemented as computer-readable storage media ("CRSM"), which may be any available physical media accessible by processor(s) 1220 to execute one or more instructions stored within memory 1224. In some embodiments, one or more applications (e.g., gaming, music, video, calendars, lists, banking, social media etc.) may be run by processor(s) 1220, and may be stored in memory 1224.

In embodiments, as mentioned above, the first electronic device 1218 and the second electronic device 1228 may include communications circuitry (communications circuitry 1226 and 1236 respectively). Communications circuitry 1226 and 1236, which may be referred to herein collectively as communications circuitry 1226, may include any circuitry allowing or enabling one or more components of the first electronic device 1218 and the second electronic device 1228 to communicate with one another, with computer system 1202, and/or with one or more additional devices, servers, and/or systems. As an illustrative example, data retrieved from the scintigraphic measurement equipment 1214 and/or the glucometric measurement equipment 1212 may be transmitted over the network 1216, such as the Internet, to the computer system 1202 using any number of communications protocols. As another illustrative example, data analyzed by the computer system 1202 may be transmitted over the network 1216 to one or more of the first electronic device 1218 and/or the second electronic device 1228 using any number of communication protocols.

For example, network 1216 may be accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between the first electronic device 1218 and the second electronic device 1228, the computer system 1202, the scintigraphic measurement equipment 1214 and/or the glucometric measurement equipment 1212. In some embodiments, the first electronic device 1218 and the second electronic device 1228, the computer system 1202, the scintigraphic measurement equipment 1214 and/or the glucometric measurement equipment 1212 may communicate with one another via a web browser using HTTP. Various additional communication protocols may be used to facilitate communications between the first electronic device 1218 and the second electronic device 1228, the computer system 1202, the scintigraphic measurement equipment 1214 and/or the glucometric measurement equipment 1212, include the following non-exhaustive list, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP.

Communications circuitry 1226 may use any communications protocol, such as any of the previously mentioned exemplary communications protocols. In some embodiments, the first electronic device 1218 and the second electronic device 1228 may include one or more antennas to facilitate wireless communications with a network using various wireless technologies (e.g., Wi-Fi, Bluetooth, radiofrequency, etc.). In yet another embodiment, the first electronic device 1218 and the second electronic device 1228 may include one or more universal serial bus ("USB") ports, one or more Ethernet or broadband ports, and/or any other type of hardwire access port so that communications circuitry 1226 allows the first electronic device 1218 and the second electronic device 1228 to communicate with one another or with one or more communications networks.

Computer system 1202 may include one or more processor(s) 1204, a network connection interface 1206 and memory 1208. In embodiments, the one or more processors(s) 1204 may be similar to processor(s) 1220 described above in connection with FIG. 12A, the description applying herein. In embodiments, the network connection interface 1206 may be similar to communications circuitry 1226 described above in connection with FIG. 12A, the description applying herein. In embodiments, memory 1208 may be similar to memory 1224 described above in connection with FIG. 12A, the description applying herein. In embodiments, computer system 1202 may include a personal data server. A personal data server may, in embodiments, be stored in memory 1208 and store the medical data observed from the subject 1238. In embodiments, computer system 1202 may be one or more electronic devices that may be mechanically, operatively, and/or electrically connected to one another.

In embodiments, the system of FIG. 12A may be used to determine whether an exemplary subject 1238 has a dyspeptic disorder or a condition associated with a dyspeptic disorder. The system of FIG. 12A, in embodiments, may make the aforementioned determination by performing the process described in connection with FIGS. 12B and 12C. In embodiments, as described above, the process described in connection with FIGS. 12B and 12C may occur over a predetermined amount of time. The predetermined amount of time may be an amount of time that a person of ordinary skill in the art would determine is necessary for the system to determine whether a subject has a dyspeptic disorder or a condition associated with a dyspeptic disorder. In embodiments, the predetermined amount of time may include a plurality of time points. For example, if the predetermined amount of time is 5 hours, the plurality of time points may include: (1) a first time point at the first hour; (2) a second time point at the second hour; (3) a third time point at the third hour; (4) a fourth time point at the fourth hour; and (5) a fifth time point at the fifth hour. While only one example is shown, a person of ordinary skill in the art understands that the predetermined amount of time may vary based on the subject, equipment, and/or medical conditions, to name a few.

FIGS. 12B and 12C are flow charts of a process for determining whether a subject has a dyspeptic disorder or a condition associated with a dyspeptic disorder. The process described in connection with FIGS. 12B and 12C, as mentioned above, may be performed by a system for classifying gastric emptying in a subject (e.g., the system described in connection with FIG. 12A). In embodiments, the process described in connection with FIGS. 12B and 12C may begin with providing the scintigraphic measurement equipment 1214, which may be configured to measure scintigraphic data of the subject's 1238 solid gastric emptying rate at a plurality of time points over a predetermined amount of time. The subject 1238, in embodiments and subsequent to the set time point, may have ingested at a set time point a meal. The meal, in embodiments, may include carbohydrate and radiolabeled protein.

The process may continue with providing the glucometric measurement equipment 1212, which may be configured to measure, from the subject 1238, glucometric data of the subject's blood glucose level at the plurality of time points subsequent to the set time point. After the measurement equipment has been provided, in embodiments, the process may continue at a step S1202. At step S1202 a plurality of control values may be stored one or more databases of a computer system. A plurality of control values, in embodiments, may include a plurality of sets of control values. For example, the plurality of sets of control values may include a first set of solid gastric emptying control values and a second set of carbohydrate gastric emptying control values, to name a few.

The first set of solid gastric emptying control values, in embodiments, may include a plurality of solid gastric emptying control values. The plurality of solid gastric emptying control values may include an upper solid gastric control value that corresponds to a time point during the predetermined amount of time and a lower solid gastric control value that corresponds to a time point during the predetermined amount of time. In embodiments, each upper and lower limit included in a set of solid gastric emptying control values may correspond to the same time point during the predetermined amount of time.

The second set of carbohydrate gastric emptying control values in embodiments, may include a plurality of carbohydrate gastric emptying control values. The plurality of carbohydrate gastric emptying control values may include an upper carbohydrate gastric control value that corresponds to a time point during the predetermined amount of time and a lower carbohydrate gastric control value that corresponds to a time point during the predetermined amount of time. In embodiments, each upper and lower limit included in a set of carbohydrate gastric emptying control values may correspond to the same time point during the predetermined amount of time.

In embodiments, the first set of solid gastric emptying control values may correspond to the same time points that the second set of carbohydrate gastric emptying control values correspond to. In embodiments, the plurality of control values may be stored in one or more of memory 1208 of computer system 1202, memory of the scintigraphic measurement equipment 1214, and/or memory of the glucometric measurement equipment 1212, to name a few.

The process of FIGS. 12B and 12C may continue at a step S1204. At step S1204, scintigraphic data for a subject is obtained by the computer system 1202. In embodiments, the scintigraphic data may be obtained for subject 1238 by the scintigraphic measurement equipment 1214 at plurality of time points of the predetermined amount of time. At each time point of the plurality of time points, in embodiments, scintigraphic measurement equipment 1214 may obtain scintigraphic data from the subject 1238. The obtained scintigraphic data may be transmitted from scintigraphic measurement equipment 1214 to the computer system 1202 via network 1216. In embodiments, the scintigraphic data may be transmitted at each time point. In embodiments, the scintigraphic data may be transmitted once all of the scintigraphic data has been obtained from the subject 1238. If the scintigraphic data is transmitted after all of the data has been obtained by the scintigraphic measurement equipment 1214, the obtained scintigraphic data may be stored on memory of the scintigraphic measurement equipment 1214 until it is ready for transmission to the computer system 1202. In embodiments, once the scintigraphic data is received by the computer system 1202, the scintigraphic data may be stored on memory 1208 of the computer system 1202.

In embodiments, the system may also obtain glucometric data from the subject. At step S1206, the computer system 1202 may obtain the glucometric data of the subject 1238 from the glucometric measurement equipment 1212. In embodiments, the glucometric data may be obtained for subject 1238 by the glucometric measurement equipment 1212 at plurality of time points of the predetermined amount of time. At each time point of the plurality of time points, in embodiments, glucometric measurement equipment 1212 may obtain scintigraphic data from the subject 1238. The obtained glucometric data may be transmitted from glucometric measurement equipment 1212 to the computer system 1202 via network 1216. In embodiments, the glucometric data may be transmitted at each time point. In embodiments, the glucometric data may be transmitted once all of the glucometric data has been obtained from the subject 1238. If the glucometric data is transmitted after all of the data has been obtained by the glucometric measurement equipment 1212, the obtained glucometric data may be stored on memory of the glucometric measurement equipment 1212 until it is ready for transmission to the computer system 1202. In embodiments, once the glucometric data is received by the computer system 1202, the glucometric data may be stored on memory 1208 of the computer system 1202.

In embodiments steps S1204 and S1206 may occur at substantially the same time.

In embodiments, the computer system 1202 may obtain a plurality of control values, which may enable the computer system 1202 to implement a machine learning technique. A machine learning technique, in embodiments, may be implemented by the computer system 1202 to accurately and/or reliably determine whether the subject 1238 has a dyspeptic disorder or a condition associated with a dyspeptic disorder. In embodiments, the machine-learning technique may be based on one or more of the following: the plurality of control values; the obtained scintigraphic data, and/or the obtained glucometric data, to name a few. The machine learning technique, in embodiments, may implement a machine learning algorithm, such as supervised learning algorithms (e.g., classification supervised learning, regression supervised learning), unsupervised learning algorithms (e.g., association unsupervised learning, clustering unsupervised learning, dimensionality reduction unsupervised learning), reinforcement learning algorithms (e.g., through trial and error), semi-supervised algorithms, Naïve Bayes Classifier Algorithm, K Means Clustering Algorithm, Support Vector Machine Algorithm, Apriori Algorithm, Linear Regression, Logistic Regression, Artificial Neural Networks, Random Forests, Decision Trees, and/or Nearest Neighbours, to name a few. In embodiments, the machine learning technique may be a deep learning technique, which may be based on learning data representations as opposed to task-specific algorithms. The deep learning technique may be supervised, semi-supervised, and/or unsupervised. In embodiments, the determination of whether the subject 1238 has a dyspeptic disorder or a condition associated with a dyspeptic disorder may be performed by using a neural network technique, which may include a deep learning neural network technique (e.g., DNN). A DNN may be an artificial neural network with multiple layers between the input (e.g., the plurality of control values; the obtained scintigraphic data, and/or the obtained glucometric data) and output (e.g., the determination of whether the subject 1238 has a dyspeptic disorder or a condition associated with a dyspeptic disorder).

In embodiments, step S1206 may include a sub-process directed towards calculating a first control range and a second control range. Referring to FIG. 13A, the sub-process of step S1206 may begin at a step S1302. At step S1302, processor(s) 1204 may calculate the first control range. The first control range, may represent an upper solid gastric emptying control rate and a lower solid gastric emptying control rate. This calculation, may be performed by the process illustrated in the flow chart shown in connection with FIG. 13B. Referring to FIG. 13B, at step S1302-1, the processor(s) 1204 may calculate the upper solid gastric emptying control rate at the plurality of time points of the predetermined amount of time. The upper limit, in embodiments, may represent the upper limit of a healthy solid gastric emptying rate of the subject 1238. The upper limit may be determined and/or calculated as discussed herein.

Continuing the calculations, at step S1302-2, the processor(s) 1204 may calculate the lower solid gastric emptying control rate at the plurality of time points of the predetermined amount of time. The lower limit, in embodiments, may represent the lower limit of a healthy solid gastric emptying rate of the subject 1238. The lower limit may be determined and/or calculated as discussed herein.

Referring back to FIG. 13A, the sub-process of step S1206 may continue at a step S1304. At step S1304, processor(s) 1204 may calculate the second control range. The second control range, may represent an upper carbohydrate gastric emptying control rate and a lower carbohydrate gastric emptying control rate. This calculation, may be performed by the process illustrated in the flow chart shown in connection with FIG. 13C. Referring to FIG. 13C, at step S1304-1, the processor(s) 1204 may calculate the upper carbohydrate gastric emptying control rate at the plurality of time points of the predetermined amount of time. The upper limit, in embodiments, may represent the upper limit of a healthy carbohydrate gastric emptying rate of the subject 1238. The upper limit may be determined and/or calculated as discussed herein.

Continuing the calculations, at step S1304-2, the processor(s) 1204 may calculate the lower carbohydrate gastric emptying control rate at the plurality of time points of the predetermined amount of time. The lower limit, in embodiments, may represent the lower limit of a healthy carbohydrate gastric emptying rate of the subject 1238. The lower limit may be determined and/or calculated as discussed herein.

Referring back to FIG. 12B, the process of determining whether a subject as has a dyspeptic disorder or a condition associated with a dyspeptic disorder may continue at a step S1208. At step S1208, the computer system 1202, using the processor(s) 1204, may access the memory 1208 to retrieve one or more of the following: the obtained scintigraphic data at the plurality of time points, the obtained glucometric data at the plurality of time points, and/or the plurality of control values, to name a few. In embodiments, the data may be accessed at substantially the same time. In embodiments, the control values may not all include upper and/or lower limits at each respective time point of the plurality of time points. In those embodiments, the process illustrated in connection with FIGS. 12B-C and 13A-13C may provide accurate and/or reliable results.

The process of FIGS. 12B and 12C may continue at a step S1210. At step S1210, first machine-readable instructions may be generated by the computer system 1202. The first machine-readable instructions, in embodiments, may be instructions to render a first graphical user interface. In embodiments, the first graphical user interface may include a first graphical representation of one or more of the following: the obtained scintigraphic data for the subject 1238 at each time point of the plurality of time points, the upper solid gastric emptying control value at each time point of the plurality of time points, and the lower solid gastric emptying control value at each time point of the plurality of time points, to name a few. The first graphical representation also plot the obtained scintigraphic data for the subject 1238 at each time point of the plurality of time points, the upper solid gastric emptying control value at each time point of the plurality of time points, and/or the lower solid gastric emptying control value at each time point of the plurality of time points, on a first graph. The first graph, may be similar to the graphs described above, the description of which applying herein.

The process of FIGS. 12B and 12C may continue at a step S1212. At step S1212, second machine-readable instructions may be generated by the computer system 1202. The second machine-readable instructions, in embodiments, may be instructions to render a second graphical user interface. In embodiments, the second graphical user interface may include a second graphical representation of one or more of the following: the obtained glucometric data for the subject 1238 at each time point of the plurality of time points, the upper carbohydrate gastric emptying control value at each time point of the plurality of time points, and the lower carbohydrate gastric emptying control value at each time point of the plurality of time points, to name a few. The second graphical representation also plot the obtained glucometric data for the subject 1238 at each time point of the plurality of time points, the upper carbohydrate gastric emptying control value at each time point of the plurality of time points, and/or the lower carbohydrate gastric emptying control value at each time point of the plurality of time points, on a second graph. The second graph, may be similar to the graphs described above, the description of which applying herein.

The process of FIGS. 12B and 12C may continue at a step S1214. Referring to FIG. 12C, at step S1214, the first machine-readable instructions may be transmitted by the computer system to a first electronic device. In embodiments, the computer system 1202 may transmit the first machine-readable instructions to the first electronic device 1218 via network 1216. When received, the first machine-readable instructions, in embodiments, may cause the first electronic device 1218 to display the first graphical user interface using display 1222. In embodiments, the computer system 1202 may transmit the first machine-readable instructions to the second electronic device 1228 via network 1216. As with the first electronic device 1218, when the second electronic device 1228 receives the first machine-readable instructions, in embodiments, the second electronic device 1228 may display the first graphical user interface using display 1232.

The process of FIGS. 12B and 12C may continue at a step S1216. At step S1216, the second machine-readable instructions may be transmitted by the computer system to a second electronic device. In embodiments, the computer system 1202 may transmit the second machine-readable instructions to the second electronic device 1228 via network 1216. When received, the second machine-readable instructions, in embodiments, may cause the second electronic device 1228 to display the second graphical user interface using display 1232. In embodiments, the computer system 1202 may transmit the second machine-readable instructions to the first electronic device 1218 via network 1216. As with the second electronic device 1228, when the first electronic device 1218 receives the second machine-readable instructions, in embodiments, the first electronic device 1218 may display the second graphical user interface using display 1222.

In embodiments, the computer system 1202 may transmit both the first and second machine-readable instructions to the same electronic device (e.g., the first electronic device 1218, the second electronic device 1228, or both the first electronic device 1218 and the second electronic device 1228). In embodiments, if the computer system 1202 transmits both the first and second machine-readable instructions to the same electronic device, the same electronic device may display both the first graphical user interface and the second graphical user interface. The first graphical user interface, in embodiments, may be displayed on a different screen or a different location on the same screen as the second graphical user interface.

The process of FIGS. 12B and 12C may continue at a step S1218. At step S1218 the processor(s) 1204 may monitor the subject's 1238 solid gastric emptying rate and the subject's 1238 carbohydrate gastric emptying rate. The monitoring, in embodiments, may be performed as the data is obtained by the computer system 1202 or once all of the data is received by the computer system 1202. In embodiments, the processor(s) 1204 may monitor the subject's 1238 solid gastric emptying rate and the subject's 1238 carbohydrate gastric emptying rate to determine at least one event of a plurality of events has occurred. In embodiments, the plurality of events may include one or more of: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion;

(v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; (ix) delayed gastric solid emptying at 2 hours postprandial and delayed blood glycemic excursion; (x) normal gastric solid emptying and elevated blood glycemic excursion; (xi) normal gastric solid emptying and delayed blood glycemic excursion; and/or (xii) normal gastric solid emptying and normal blood glycemic excursion, to name a few.

If, in embodiments, the computer system 1202 determines at least one event has occurred, the computer system 1202 may generate an alert based on the at least one event.

The process of FIGS. 12B and 12C may continue at a step S1220. At step S1220 the computer system 1202, in response to determining at least one event has occurred, may transmit the generated alert to at least one of the first electronic device 1218 and the second electronic device 1228. The alert may, in embodiments, indicate at least one of the following: (1) the subject 1238 has a dyspeptic disorder; (2) the subject 1238 has a condition associated with a dyspeptic disorder; (3) the subject 1238 does not have a dyspeptic disorder; and/or (4) the subject 1238 does not have a condition associated with a dyspeptic disorder. In embodiments, the alert may indicate that the subject 1238 has either a dyspeptic disorder or a condition associated with a dyspeptic disorder if the determined at least one event is one or more of the following: (i) rapid gastric solid emptying and elevated blood glycemic excursion; (ii) rapid gastric solid emptying and normal blood glycemic excursion; (iii) rapid gastric solid emptying and delayed blood glycemic excursion; (iv) delayed gastric solid emptying at 4 hours postprandial and elevated blood glycemic excursion; (v) delayed gastric solid emptying at 2 hours postprandial and normal blood glycemic excursion; (vi) delayed gastric solid emptying at 2 hours postprandial and delayed blood glycemic excursion; (vii) delayed gastric solid emptying at 2 hours postprandial and elevated blood glycemic excursion; (viii) delayed gastric solid emptying at 2 hours postprandial and normal blood glycemic excursion; (ix) delayed gastric solid emptying at 2 hours postprandial and delayed blood glycemic excursion; (x) normal gastric solid emptying and elevated blood glycemic excursion; and/or (xi) normal gastric solid emptying and delayed blood glycemic excursion. In embodiments, the alert may indicate that the subject 1238 does not have either a dyspeptic disorder or a condition associated with a dyspeptic disorder if the determined at least one event is normal gastric solid emptying and normal blood glycemic excursion.

The steps of the processes described above in connection with FIGS. 12B-C and 13A-C may be rearranged or omitted.

In embodiments, the methods can be performed serially. In embodiments, the methods allow assessment of gastric emptying in a subject in a shorter time period than previously possible with prior art methods.

A predetermined value is a value decided or determined beforehand. E.g. a predetermined value in a method is a value decided before a method is effected by a user. Predetermined upper values and lower values can be, respectively, in embodiments, upper normal limit and the lower normal limit for gastric emptying. Such values are available in the literature and are familiar to those in the art, or can be determined from a control subject or can be determined from a control population. Predetermined upper blood glucose levels and lower normal glucose can be, respectively, in embodiments, normal upper blood glucose levels and normal lower blood glucose levels. Such values are available in the literature and are familiar to those in the art, or can be determined from a control subject or can be determined from a control population.

Prediabetes is a condition known in the art wherein a subject's blood sugar level is higher than normal but not high enough to be classified as type 2 diabetes.

Gastroparesis is a condition known in the art wherein that affects the normal spontaneous movement of the muscles/motility a subject's stomach. In gastroparesis, the stomach's motility is either slowed or absent, preventing your stomach from emptying properly.

Dyspepsia is a condition known in the art wherein discomfort in the subject's upper abdomen is apparent, or sometimes the pain can be manifest anywhere in the abdomen. For example, patients with malabsorption have bloating, cramps, diarrhea and mid and lower abdominal pain. It can be referred to as indigestion. Symptoms often also include a feeling of fullness soon after ingestion of food.

Solid gastric emptying as measured by radiolabeled-protein meal scintigraphy can be considered an indication of protein emptying since the radio-activity measured is from particles bound to proteins of the meal. Carbohydrate gastric emptying can be measured directly as measured by radio-labeled-carbohydrate containing meal scintigraphy or can be indirectly measured from blood glucose levels.

In embodiments, where a numerical range is provided herein, it is understood that all numerical subsets of that range, and all the individual integers contained therein, are provided as embodiments of the invention. For example, 30 to 70 includes the subset of 30 to 35, the subset of 40-60, etc. as well as every individual integer value, e.g. 30, 31, 32, 33, and so on.

"And/or" as used herein, for example with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention and embodiments thereof will be better understood from the Experimental Details, which follow. However, one skilled in the art will readily appreciate that the specific methods and results discussed are merely illustrative of embodiments of the invention as described more fully in the claims that follow thereafter.
Experimental Details The inventors considered that the unlabeled carbohydrate component of the standardized GES egg meal could empty more rapidly than the radiolabeled protein component, and that this rapid carbohydrate emptying may lead to variable gastric emptying effects not detected with current imaging methods. It was hypothesized that abnormally rapid carbohydrate emptying, alone or in combination with abnormal gastric emptying for protein, may be an unidentified cause of postprandial gastrointestinal symptoms.

In the current study, serial blood glucose measurements during gastric emptying scintigraphy were utilized as a surrogate marker for gastric emptying patterns of the unlabeled carbohydrate components in the standardized radiolabeled egg-white meal. It has been reported the rate of carbohydrate gastric emptying is highly correlated with 30 minute and 1 hour postprandial glucose excursions above baseline (7-12). In a study of normal subjects, the postprandial glucose excursions were significantly correlated with the gastric emptying at 30 minutes (R=−0.58, p<0.05) (8) and in another study, diabetic subjects had 1 hour blood glucose excursions that significantly correlated with gastric half emptying times (R=−0.65, P=0.0001) (9). In a prior study by the present group, all normal and diabetic patients with post-prandial serum glucose excursions of >75 mg/dL above their fasting baseline levels at 30 minutes were found to have abnormally rapid gastric emptying of a liquid carbohydrate meal composed of a flavored glucose solution having an osmolality (0.62 molar) similar to commercial juice and soda beverages. On the other hand, all subjects with normal gastric emptying rates had glucose excursions of <60 mg/dL at 30 minutes and 1 hour (12).

Herein, 197 consecutive patients were reviewed that referred to our clinic for a solid standardized radiolabeled egg white, toast and jam GES who also had simultaneous fingerstick blood glucose measurements performed at each time point of acquisition of the gastric scintigraphy images (baseline, 0.5, 1, 2 and 4 hours) using methodology described in a consensus statement for the standardized egg-white meal by the nuclear medicine and gastroenterology societies (1).

Methods

A retrospective analysis was performed on 197 consecutive patients referred for GES for evaluation of postprandial abdominal pain or other gastrointestinal symptoms such as vomiting and bloating. For comparative purposes, consecutive patients were excluded from this retrospective review if they did not complete consumption of 100% of the standardized solid radiolabeled egg-white meal. Approval to perform this retrospective review was given by the University of Texas HSC-San Antonio IRB and University Hospital, San Antonio under protocol number HSC-20140318H. All patients were given the standardized solid $^{99m}$TC-SC radiolabeled egg-white meal containing 120 grams of egg-white (61 kcal), 2 slices of white bread (120 kcal) and 30 grams of strawberry jam (74 kcal, total kcal content of 255 kcal) radiolabeled with 1 mCi $^{99m}$TC-SC with imaging performed according to the 2007 ACR-SNM-SPR Practice Guideline for the Performance of Gastrointestinal Scintigraphy based on international control values (6). Static 1 minute images were performed in the anterior and posterior positions with regions of interest drawn around the stomach in the anterior and posterior positions and geometric mean calculation of the percent retained in the stomach was performed. Importantly, on the first set of anterior and posterior images acquired immediately after meal consumption, a region of interest was drawn around both the stomach and the whole abdomen on both the anterior and posterior images to determine the amount of meal emptied during the time of meal consumption. Additionally, all patients had blood glucose measurements performed by finger stick glucometer prior to meal consumption and at 0.5, 1, 2 and 4 hours post-meal consumption. The collection of postprandial glucose measurements are a standard part of our clinical practice which was suggested as a likely future addition to gastric emptying scintigraphy in the Joint Report of the Consensus Recommendations for Gastric Emptying article in Table 2, and in manuscript section 3.D. and under Items for Future Investigation, with subtitle Glycemic Control (1,13). Blood glucose measurements were made immediately prior to acquisition of one minute planar anterior and posterior gastric scintigraphy.

Patients were classified as having normal, rapid or delayed solid gastric emptying based on criteria specified in the standardized $^{99m}$TC-SC solid meal gastric emptying protocol (1). According to this convention, "delayed" gastric emptying is defined as having more than 10% of the meal remaining in the stomach at 4 hours. Based on criteria for the standardized solid meal, patients were classified as having rapid solid gastric emptying if they emptied >30% of the meal at 30 minutes and/or >70% of the meal at 1 hours, delayed gastric emptying at 4 hours if they emptied <90% of the meal and delayed emptying at 1 and 2 hours only if they emptied <10% of the meal. Patients were further sub-categorized according to postprandial glycemic excursions above baseline at 30 minutes or 1 hour. A postprandial glucose was considered to be "elevated" if the glycemic excursion above baseline was >75 mg/dL @30 minutes or >85 mg/dL @ 1 hour. A postprandial glycemic excursion was considered "normal" if the elevation above the fasting baseline was >30 mg/dL but <75 mg/dL @30 minute; or >30 mg/dL but <85 mg/dL @ 1 hour. Patients were classified as having a "diminished" glycemic excursion if the serum glucose elevation at 30 minutes was <30 mg/dL above baseline glucose levels. These criteria for postprandial glycemic excursions were based on prior studies published by our group measuring both gastric emptying and postprandial glycemic excursions in diabetic and normal patients who were administered a liquid carbohydrate glucose meal (7,12). When classification was independently applied to the 197 GES results, all 3 readers were independently in agreement with the individual GES and glucose assessments. Additionally, patient-specific symptoms were recorded before and during all imaging time points and ranked on a scale of 1-10 with 1 being mild nausea or discomfort and 10 being the most severe nausea or discomfort. These symptom patterns are depicted in the individual patient examples of FIGS. 2-8 but they have not been systematically analyzed in this paper.

During the last half of the time period for these GES studies, patients who were noted to have either normal or delayed gastric emptying while also having an elevated glycemic excursion, were recommended to return for an additional liquid glucose GES study. Seven of these patients were type 2 diabetics and 2 were non-diabetic. This second study was performed at the option of the referring doctor although performance of both solid and liquid gastric emptying studies in the same patient is a common practice in some nuclear medicine clinics. During this time, nine patients with normal or delayed gastric emptying also in addition to abnormally elevated glycemic excursions were referred back for a follow up liquid glucose carbohydrate gastric emptying study. The liquid glucose meal was composed of 50 grams of glucose in 450 mL of water (200 kcal, 0.62 molar) containing 1 mCi $^{99m}$TC-SC. Normal gastric emptying rates for this liquid glucose meal protocol were previously described in prior studies published by our group (7, 12, 14). Comparisons of the standardized egg white GES to the liquid glucose GES results in each of these 9 patients were analyzed using normal gastric emptying parameters for each meal. Means and standard deviations of GER, along with normal parameters, were plotted for each study. Postprandial glycemic excursions were also compared between the standardized solid meal and the liquid glucose meal and statistically analyzed using paired t-testing.

Results

The results are shown in FIG. 1. Of the 197 consecutive patients referred for gastrointestinal symptoms, 112 were diabetic and 75 were non-diabetic. One hundred and five patients had normal solid gastric emptying, 54 patients had delayed solid emptying at 4 hours, 13 patients had initially delayed solid emptying 1 or 2 hours with normal solid emptying at 4 hours and 25 patients had rapid solid emptying based on the classification for solid gastric emptying of standardized solid egg-white meal with results shown in Table 1.

TABLE 1

| Solid Gastric Emptying Results in 197 Consecutive Patients Classified by Standardized Low Fat Egg-White Meal Criteria | |
| --- | --- |
| Rapid solid emptying (>30% emptied at 0.5 hour and >70% emptied at 1 hour) | 25 |
| Normal solid emptying (<30% emptied at 0.5 hour and <70% emptied at 1 hour and >90% emptied at 4 hours) | 105 |
| Delayed emptying at 4 hours (<90% emptied at 4 hours) | 54 |
| Delayed emptying at 1 or 2 hours but normal emptying at 4 hours. (<10% emptied at 1 hour and/or <40% emptied at 2 hours, but >90% at 4 hours) | 13 |

One hundred and one (101) patients out of the 197 patients had elevated glycemic excursions. Of these patients, 70.5% were diabetics and 29.3% were non-diabetics (Table 2). There were 105 patients with normal gastric emptying with 58 of these patients having elevated postprandial glycemic excursions, 47 having normal glycemic excursions and none had minimal glycemic excursions. Of the 54 patients with delayed gastric emptying (at 4 hours), 26 had elevated glycemic excursions, 16 had normal glycemic excursions and 12 patients had diminished glycemic excursions with results shown in FIG. 1. There were 13 patients with initially delayed gastric emptying at 1 or 2 hours but normal gastric emptying at 4 hours with 2 patients having elevated glycemic excursions, 11 having normal glycemic excursions and none had diminished glycemic excursions. A majority of the 25 patients with rapid solid gastric emptying had abnormally elevated glycemic excursions (15 patients), while 8 had normal glycemic excursions and 2 patients had diminished glycemic excursions.

TABLE 2

| Classification of patients with elevated glycemic excursions for diabetes and solid emptying rate 101 out of 197 consecutive patients | | |
| --- | --- | --- |
| Solid emptying | Diabetic | Non-Diabetic |
| Rapid solid emptying (15 of 25) | 8 | 7 |
| Normal solid emptying (58 of 105) | 47 | 11 |
| Delayed solid emptying 4 hours (26 of 54) | 22 | 4 |
| Delayed solid emptying at 1 and 2 hours (2 of 13) | 2 | 0 |
| % of patients | 70.5% | 29.5% |

Figure 2:
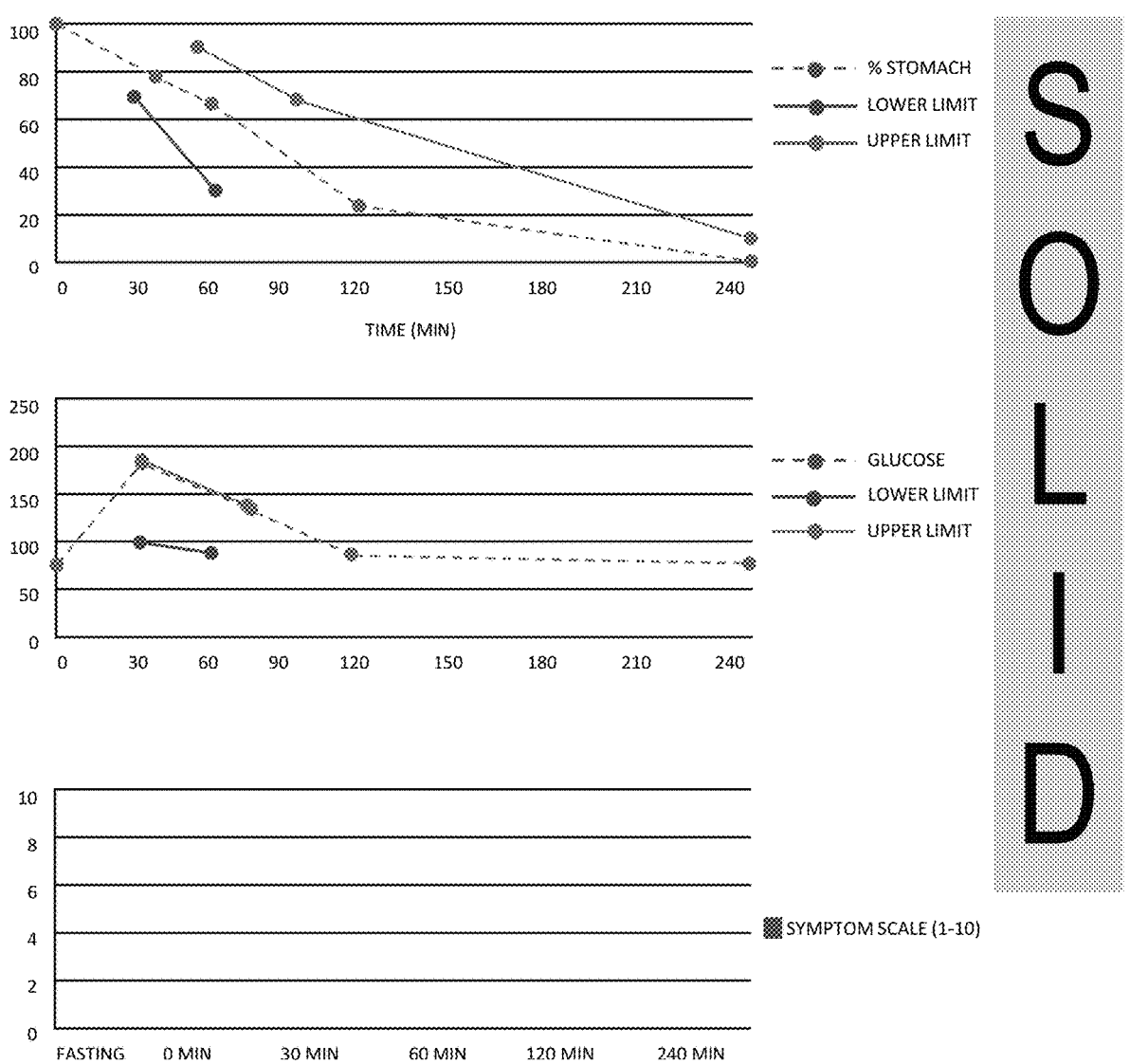
FIG. 2: Example of a typical non-diabetic patient with normal solid gastric emptying and a normal postprandial glucose excursion.
Figure 3:
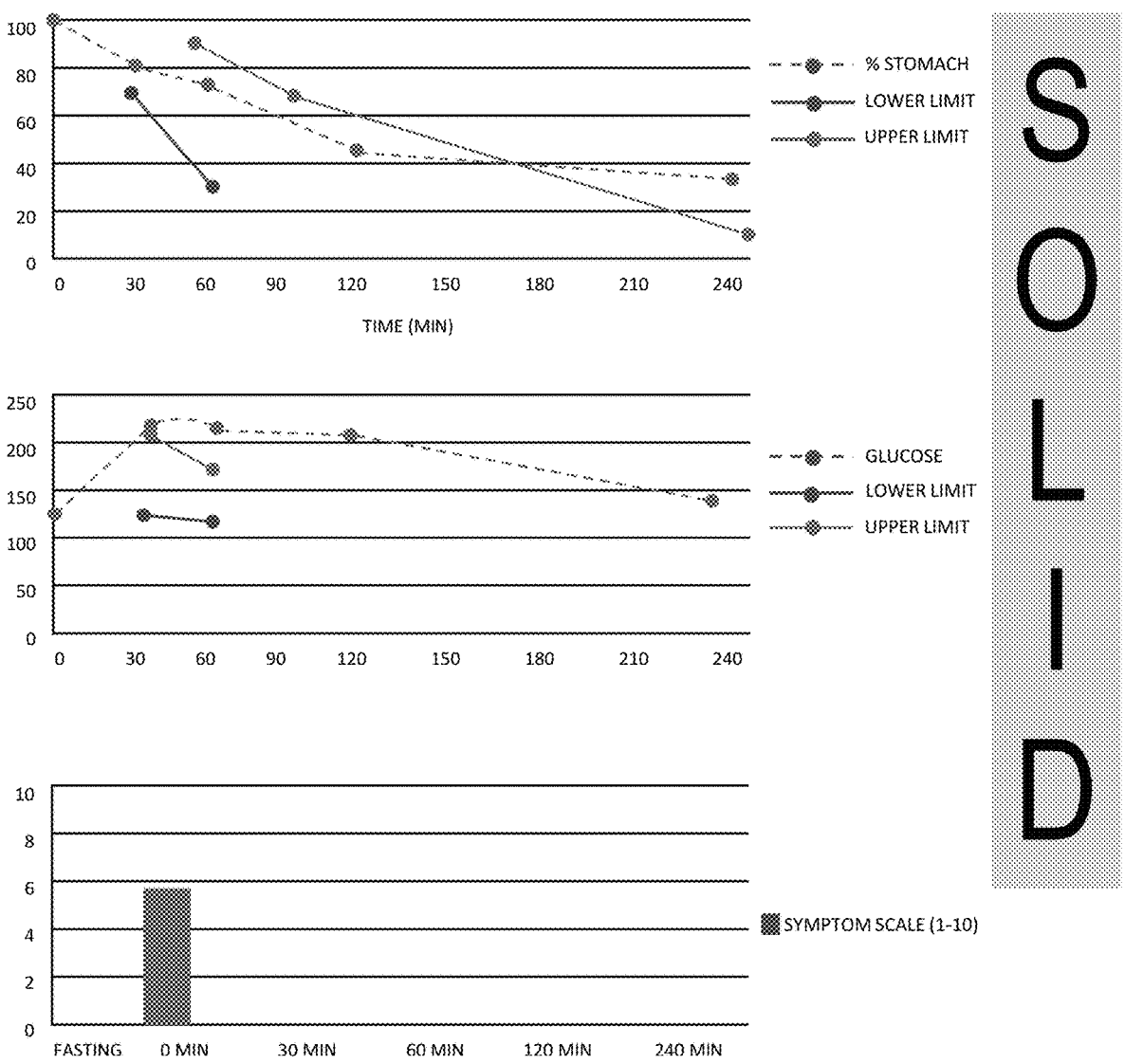
FIG. 3: Example of patient with delayed solid gastric emptying and an elevated glycemic excursion of 97 mg/dL. The prolonged elevation of glucose levels may be causing an abnormally elevated glucose "feedback gastroparesis" with 33% of the ingested meal remaining in the stomach at 4 hours. During this study, the patient had significant pain (6/10) immediately after eating the complete meal. This patient's postprandial glucose excursions above baseline of 78 mg/dL at 30 minutes and 97 mg/dL at 1 hour are consistent with rapid carbohydrate emptying.
Figure 4:
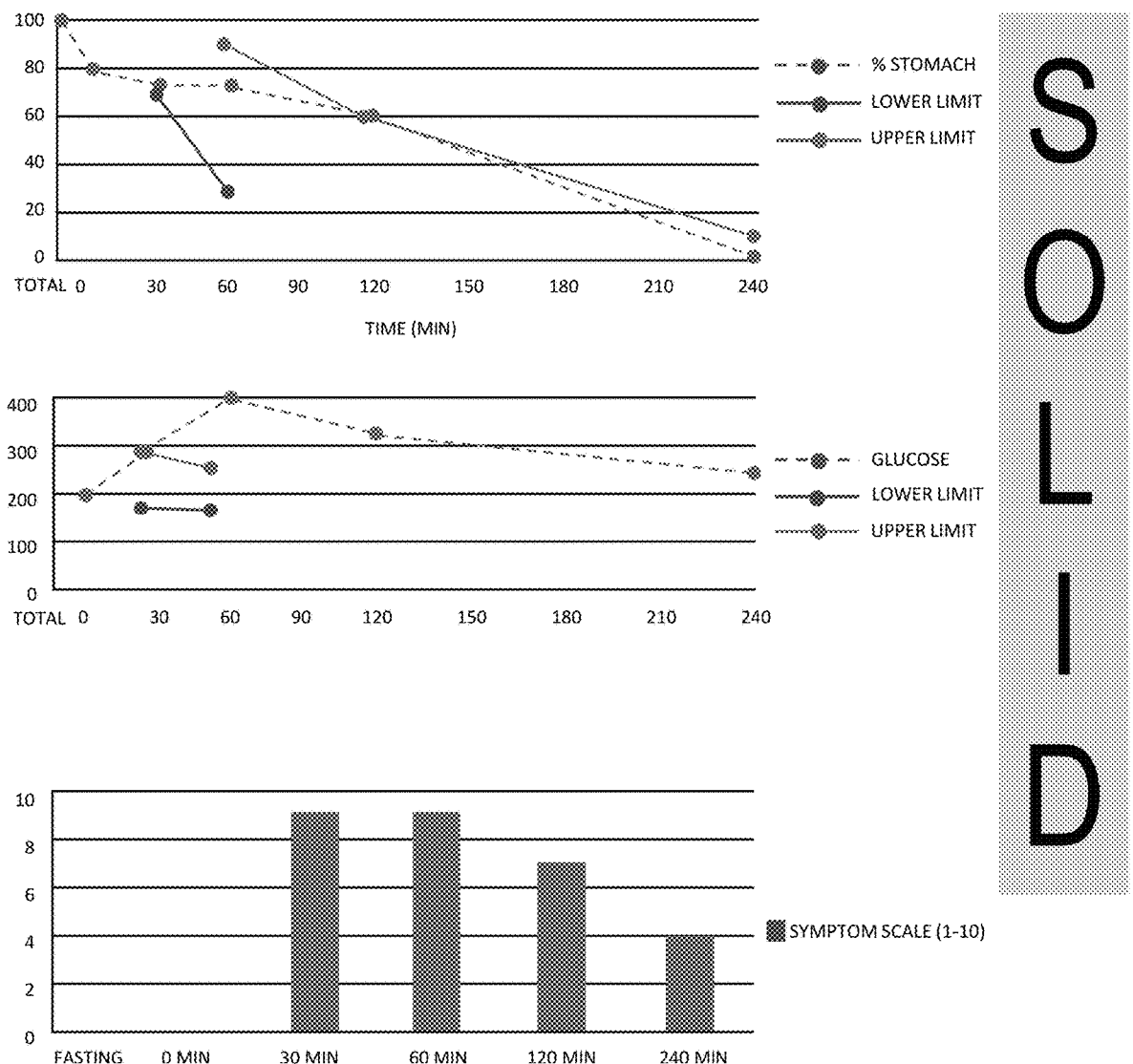
FIG. 4: This study is an example of a patient with delayed solid gastric emptying at 2 hours which normalized at 4 hours. Note the very significantly elevated postprandial glycemic excursion above baseline at 30 minutes (86 mg/dL) and at 1 hour (193 mg/dL) associated with 9 out of 10 pain at 30 minutes and 1 hour. Also, note the pause in gastric emptying from 30 minutes to 1 hour which normalized by 4 hours when blood glucose levels approached baseline levels.
Figures 5A, 5B:
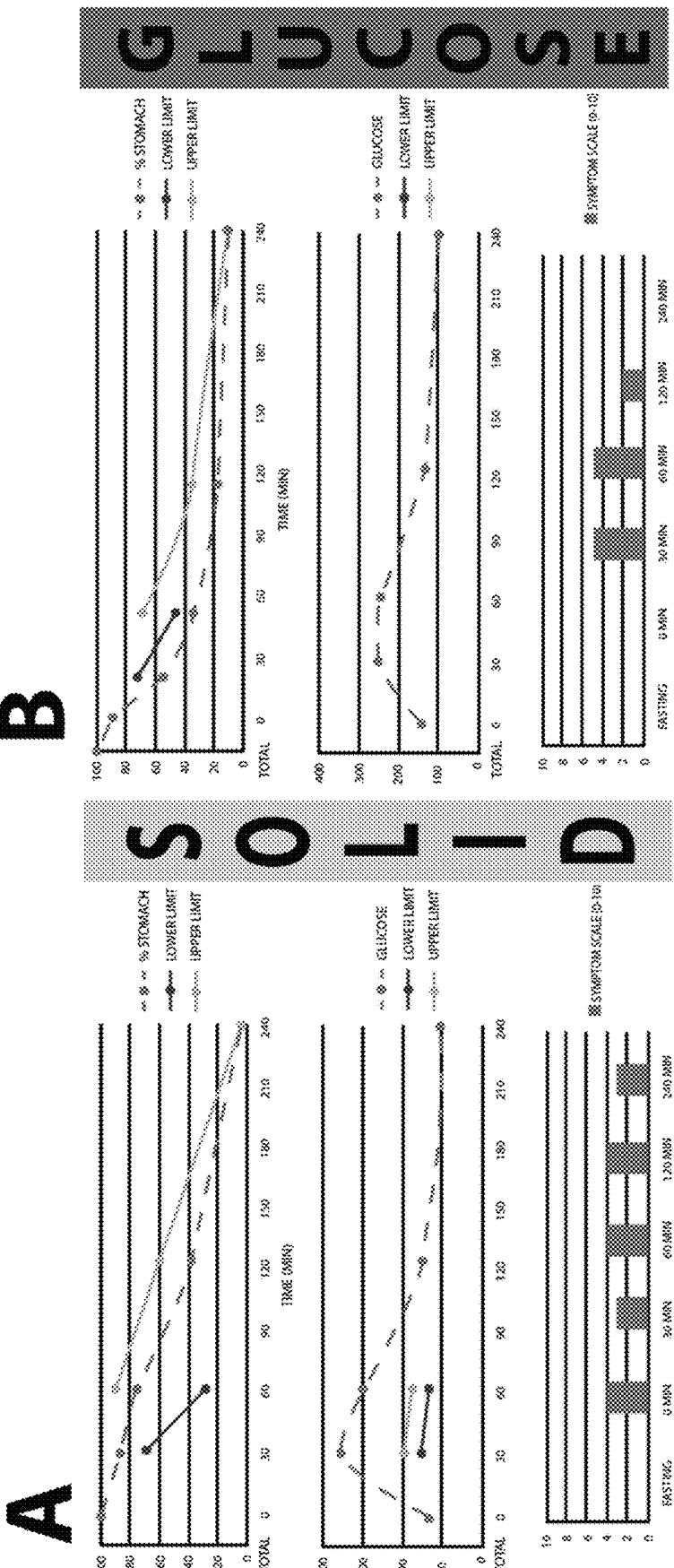
FIG. 5A-5B: Example of a patient with normal solid gastric emptying while also having significantly elevated postprandial glycemic excursion consistent with rapid carbohydrate emptying (5A). This patient was followed up with a liquid glucose gastric emptying study which was abnormally rapid. During both the solid and the liquid gastric emptying study, the patient had significant postprandial pain within the first hour after meal consumption (5B).
Figure 6:
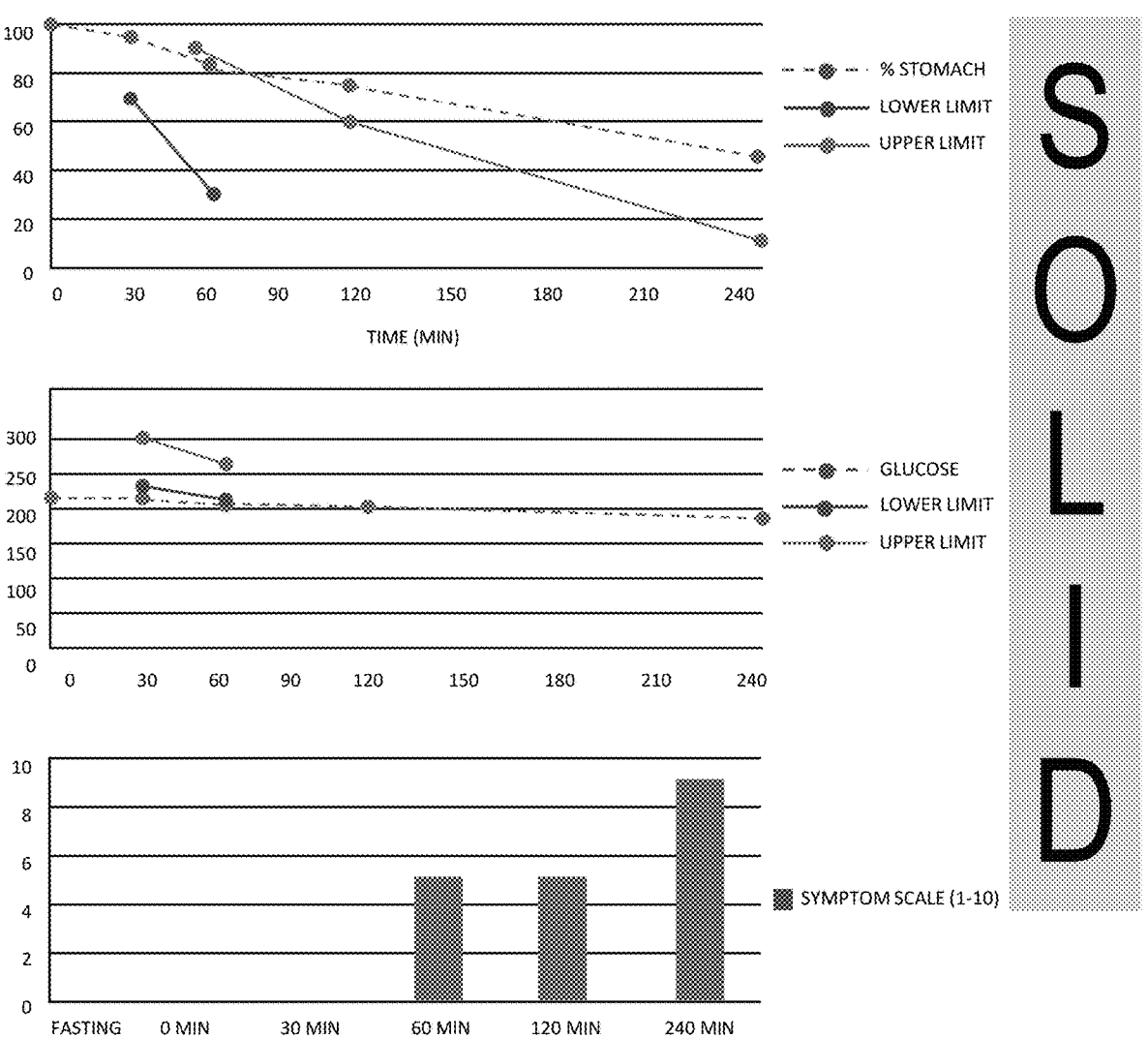
FIG. 6: Example of a diabetic subject with delayed solid gastric emptying and diminished postprandial glycemic excursion indicative of delayed carbohydrate gastric emptying with associated with delayed pain symptoms consistent with neuropathic gastroparesis.
Figure 7:
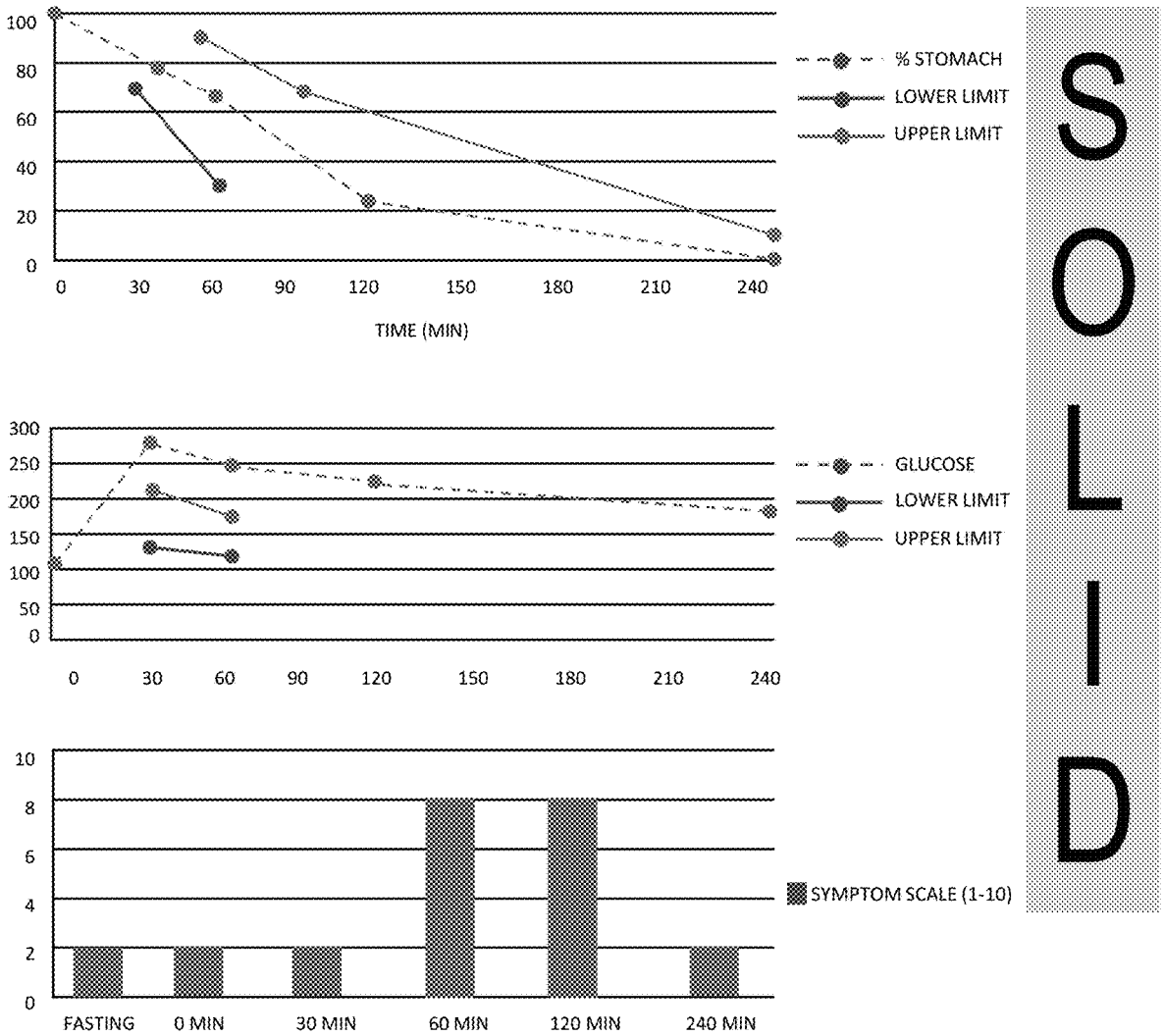
FIG. 7: Example of a diabetic patient with rapid solid gastric emptying and an elevated glycemic excursion associated with early postprandial pain.
Figure 8:
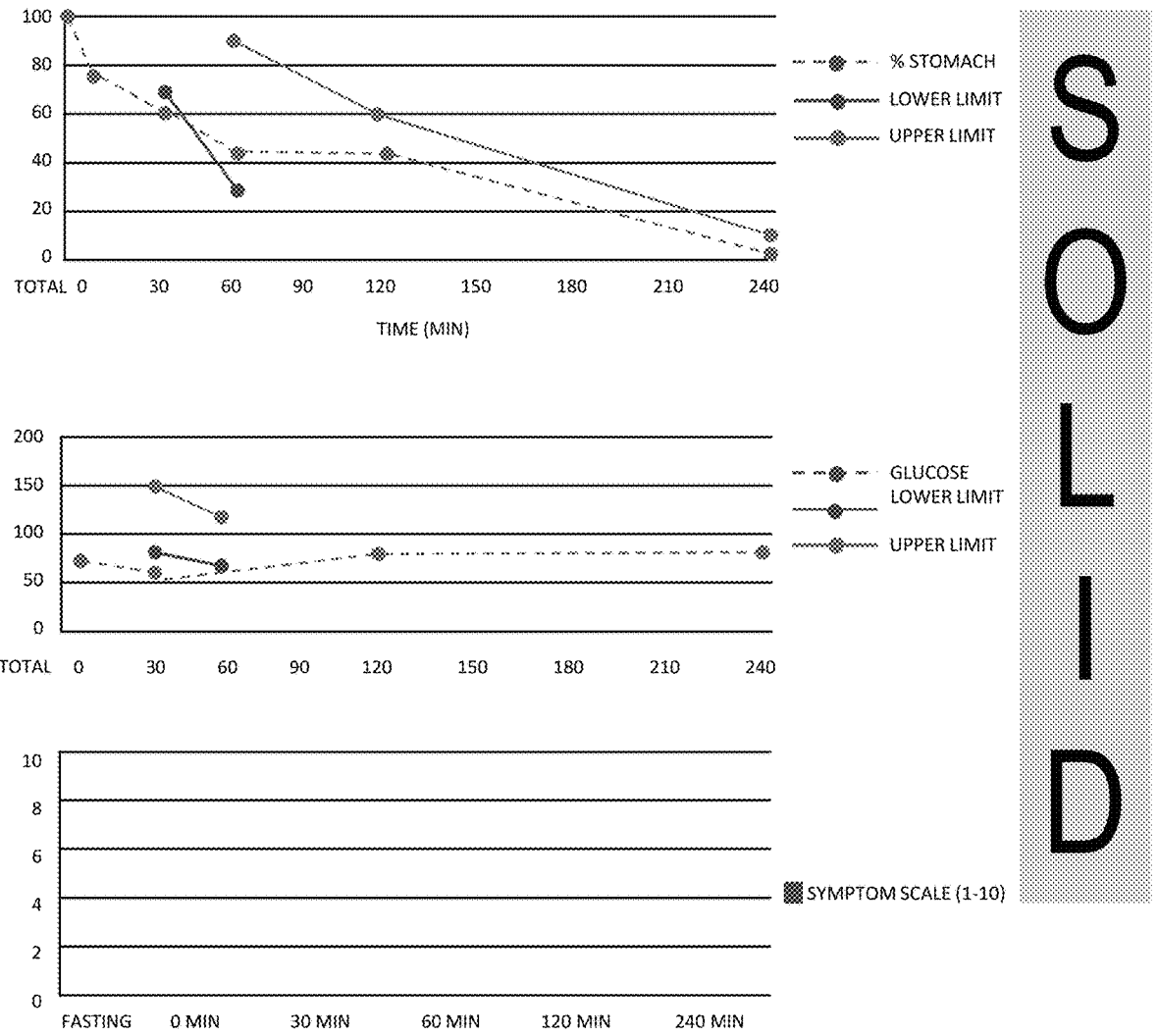
FIG. 8: Rapid initial solid gastric emptying with a significantly diminished glucose excursion consistent with malabsorption. Two of the 197 patients in this study had this pattern of rapid gastric emptying and a significantly diminished glycemic excursion. Both of these patients complained of bloating and diarrhea.

Forty seven of the 197 patients had normal solid gastric emptying and normal glycemic excursions. A typical patient with normal gastric emptying study and normal postprandial glycemic excursion is shown in FIG. 2. Fifty-four patients had delayed GES results. Nearly 50% (26/54) of these patients with delayed GES also had elevated postprandial glucose excursions. An example of a patient with this pattern is shown in FIG. 3. Thirteen of the 197 patients had initially delayed gastric emptying (at 1 and/or 2 hours but normal gastric emptying at 4 hours) with a typical patient shown in FIG. 4. In contrast, FIG. 5A shows an example of a patient with a normal solid gastric emptying rate but an abnormally elevated glycemic excursion which was further assessed with a liquid glucose gastric emptying study. This patient, one of the 9 who returned for the dual assessments of GES techniques (FIG. 5B), demonstrated an abnormally rapid GES which would have been undetected using standard protocols for GES. These data support the likely association of elevated solid meal glycemic excursions within the first hour with rapid emptying of the non-labeled carbohydrate containing components contained in the solid meal. An example of a patient with delayed solid emptying and an abnormally diminished glycemic excursion is shown in FIG. 6. This pattern is most likely associated with delayed gastric emptying of the carbohydrate meal components as well as the protein meal component which would be expected with a vagal neuropathy. Lastly, twenty five of the 197 patients had rapid solid gastric emptying. An example of a patient with rapid solid gastric emptying is shown in FIG. 7. Only 2 of the 197 patients had abnormally rapid solid gastric emptying and an abnormally diminished glycemic excursion as shown in FIG. 8. This pattern is consistent with patients who have malabsorption of the carbohydrate portion of the standardized meal. Interestingly, both of these patients complained of significant bloating and diarrhea.

Figure 9:
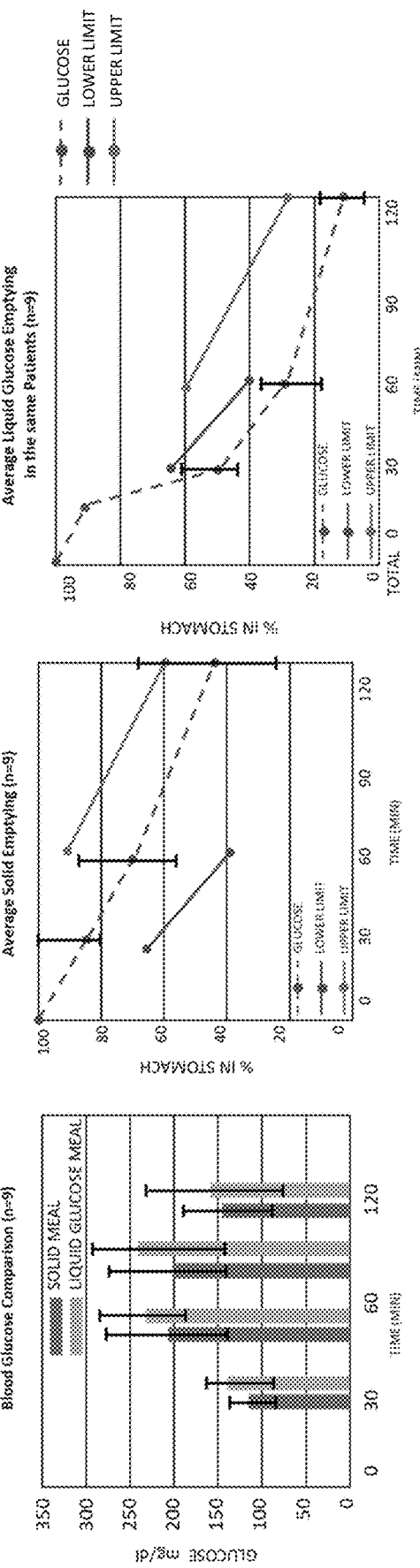
FIG. 9: All of these 9 patients (7 diabetic and 2 non-diabetic) had abnormally elevated glucose excursions during the solid meal as well as during the liquid glucose meal. Note that the postprandial glucose excursions were very similar and which were not significantly different between the solid meal and the liquid glucose meal. All of these patients had abnormally rapid liquid glucose gastric emptying as compared with established normal liquid glucose gastric emptying rates while the gastric emptying of the radiolabeled protein or delayed was normal in these patients.
Figure 10:
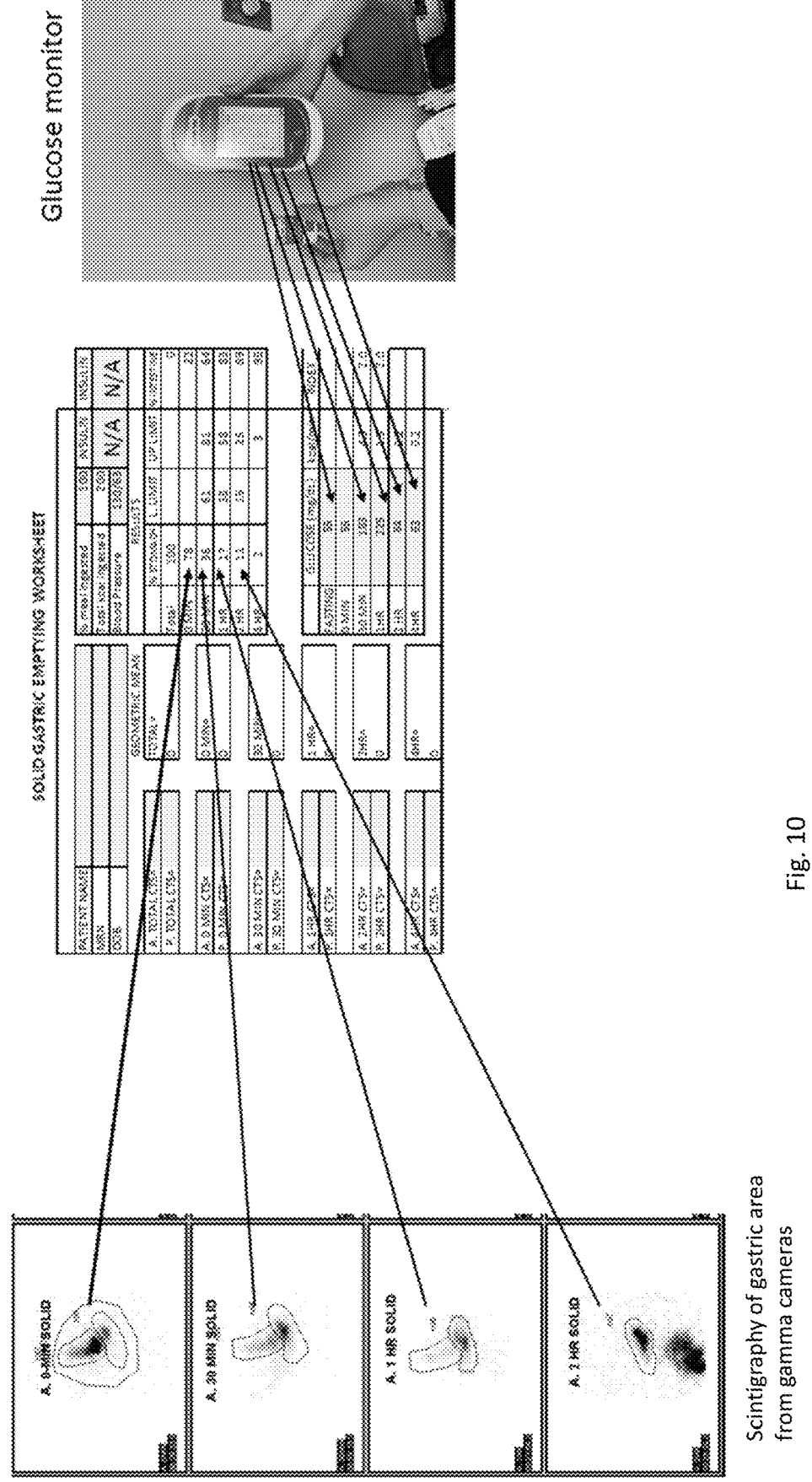
FIG. 10: Automated movement of region of interest quantitation data from nuclear processing station and glucometric data from glucometer into spreadsheet for analysis.
Figure 11:
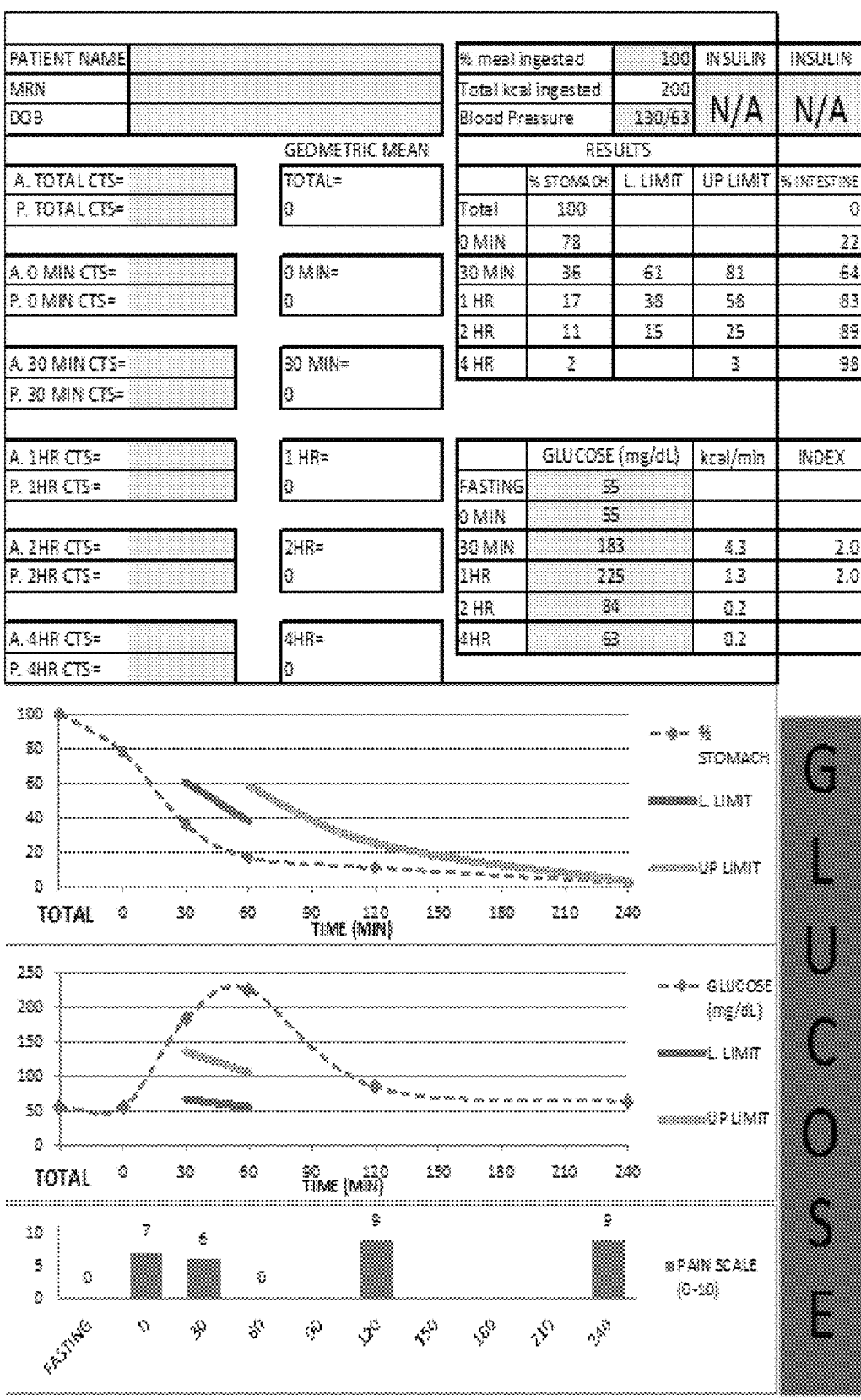
FIG. 11: Exemplary physician's report display—data automatically displayed and radioactively decay corrected. Expected normal value parameters are plotted and normal/standard values automatically corrected for total kcal ingested with sliding scale adjustment for patients who do not consume the whole meal.

In summary, 9 patients with either normal or delayed gastric emptying who were also having elevated postprandial glucose excursions during the first hour were referred back for further assessment using liquid glucose GES to investigate our concerns that an elevated glycemic excursions may lead to otherwise undetected rapid rates of isolated carbohydrate gastric emptying. Comparison of the average glycemic excursions between the two meals are shown in FIG. 9A. All nine of these patients were found to have rapid liquid glucose carbohydrate gastric emptying with abnormally elevated postprandial blood glycemic excursions which were not significantly different between the glucose and the solid meal, (p=0.3 at 30 minutes, p=0.19 at 1 hour and p=0.73 at 2 hours) as shown in FIG. 9A. Average gastric emptying of the solid meal in the 9 patients was within normal limits as shown in FIG. 9B. Abnormally rapid average gastric emptying of the liquid glucose meal for these same 9 patients is shown in FIG. 9C. Note the exponential pattern of emptying of the liquid glucose meal, similar to the exponential pattern expected gastric emptying of water, even though this liquid glucose meal has been previously reported to empty in a linear fashion in normal, non-symptomatic subjects (14).

Discussion

The association between gastric emptying abnormalities and patient's gastrointestinal symptoms remains sub-optimally understood and it is well known that gastric emptying studies have not always correlated well with patient symptoms (15-18). Based on our current study, it is likely that at least one factor underlying the poor correlation between gastric symptoms and the rate of gastric emptying may be related to unrecognized abnormal gastric emptying of unlabeled meal components. Our study suggests a significant number of patients with normal or delayed gastric emptying of the solid egg-white meal component may have rapid emptying of the carbohydrate meal components. Eighty six out of 172 patients with normal or delayed solid gastric emptying also had an abnormally elevated postprandial glycemic excursion. Surprisingly, 26 of the 54 patients with delayed solid emptying were also shown to have an abnormally elevated glycemic excursion consistent with these patients having rapid carbohydrate emptying during the first hour of the study which was then followed by delayed emptying of the radiolabeled solid egg-white meal component.

In this study, it was an unexpected result to find that more than 50% of all the patients had an abnormally elevated glycemic excursion with the standardized egg-white, bread and jam meal. Although it is possible that some of these patients have severe insulin resistance as a cause of their elevated postprandial glycemic excursions, prior studies have shown that high glycemic excursions within the first hour are commonly associated with rapid gastric emptying of carbohydrate meal components (8, 12). Rapid gastric emptying of carbohydrates has been previously reported to be common in diabetic patients (12, 19-21) and this may explain the high percentage of patients with elevated glycemic excursions in our study since the majority of our patients had diabetes (Table 2). In this study, almost 30% of the non-diabetic subjects also had elevated glycemic excursions. These non-diabetic patients are likely at increased risk of developing diabetes as several studies have suggested that non-diabetic patients with rapid gastric emptying and elevated postprandial glycemic excursions are at increased risk developing diabetes (11, 12). These non-diabetic subjects may have metabolic syndrome as prior studies by our group have shown that patients with markers of metabolic syndrome have more rapid gastric emptying (7, 22).

It may be expected the different meal components could potentially empty at different rates, knowing that fats, proteins and carbohydrates are digested by different enzymes and their rate of gastric emptying is controlled by different incretin hormones secreted from small intestine incretin cells (2). Carbohydrates are typically digested and triturated into liquid form more rapidly than proteins (17). The antropyloric contractions in conjunction with partial opening and closing of the pylorus result in a "sieving effect" in which small particles continuously flow from the stomach to the duodenum, whereas the larger particles are retropelled and retained in the stomach for further digestion (3). As previously discussed, it is also true that different meal macronutrients are under different hormonal controls (4).

Based on the observations in this study, it appears the majority of patients would benefit from having an isolated carbohydrate meal GES in addition to the standardized solid egg-white meal GES for a more comprehensive characterization of their gastric emptying. Alternatively, it may be possible to develop a dual isotope radiolabeled meal protocol enabling the carbohydrate and protein components of the meal to be tracked separately during the same meal. Dual isotope gastric emptying studies have already been described using $^{99m}TC$-sulfur colloid to label minced beef and $^{113}In$ diethylenetriaminepentaacetic acid (DTPA) or $^{67}Ga$ Ethylenediaminetetraacetic acid (EDTA) to label 10% dextrose, although the small molecules can track liquid glucose but not bread carbohydrates. (16).

Simultaneous blood glucose monitoring during the gastric emptying study appears to be a valuable addition to the standardized GES protocol which is inexpensive and relatively easy to perform. Monitoring postprandial glycemic excursion appears to provide a useful indicator for the emptying of the unlabeled carbohydrate component in the standardized meal. All 9 patients who returned for liquid glucose GES had abnormally elevated carbohydrate gastric emptying. As shown in this study, glucose monitoring during the standardized solid egg-white meal gastric emptying study can screen patients for rapid gastric emptying of unlabeled carbohydrate meal components. Postprandial glucose levels can also clarify a neuropathic pattern of gastric emptying in which an abnormally diminished glycemic excursion is consistent with both the carbohydrate meal component and the radiolabeled egg white having delayed gastric emptying as would be expected for gastroparesis due to vagal nerve deterioration. The early postprandial symptoms noted in many of the patients with elevated glycemic excursions are similar to symptoms observed in patients with functional dyspepsia. The global prevalence of functional dyspepsia is between 5-11 percent with medical costs associated with this condition in excess of 18 billion dollars per year (23,24) yet its pathophysiology remains poorly understood (25). The cause and mechanisms of functional dyspepsia are controversial. Although functional dyspepsia has previously been assumed to be associated with delayed gastric emptying (26) pro-motility agents have not been very effective for its treatment (23, 25). Several studies over the last decade have reported functional dyspepsia can be associated with rapid gastric emptying (15, 27, 28).

Gastric emptying studies determined to be delayed, may in fact, have a rapid emptying carbohydrate component contributing to the patient's symptoms thus obscuring the clinical picture and sub-optimizing clinical management. These patients may have a "feedback gastroparesis" caused by elevated glucose levels leading to a delayed emptying of the radiolabeled solid meal component. This feedback gastroparesis is possible because blood glucose is an important regulator of gastric emptying (16, 29-31). Schvarcz et al. performed a study in which induced hyperglycemia with an intravenous glucose clamp was associated with significantly delayed gastric emptying (31). The high number of patients in this study with elevated postprandial glycemic excursion while also having delayed solid gastric emptying may provide some clues to the confusion and controversy surrounding the causes of gastroparesis (32). In our study, patients with delayed solid gastric emptying were twice as likely to have elevated glycemic excursions in the first hour as to have diminished glycemic excursions.

The monitoring of glucose during the standardized gastric emptying study can provide valuable information for assessing each patient and developing a patient management plan. The additional insights provided by fingerstick glucose monitoring are inexpensive, easy to perform and may provide for new approaches to management of patient's gastrointestinal symptoms.

The exemplary embodiments of the present invention, as set forth above, are intended to be illustrative, not limiting. The spirit and scope of the present invention is to be construed broadly.

REFERENCES

1. Abell T L, Camilleri M, Donohoe K, et al. Consensus recommendations for gastric emptying scintigraphy: a joint report of the American Neurogastroenterology and Motility Society and the Society of Nuclear Medicine. *Am J Gastroenterol.* 2008; 103:753-763.
2. Weiner K, Graham L S, Reedy T, et al. Simultaneous gastric emptying of two solid foods. *Gastroenterology.* 1981; 81:257-266.
3. Kong F, Singh R P. Disintegration of solid foods in human stomach. *J Food Sci.* 2008; 73:R67-80.
4. Pais R, Gribble F M, Reimann F. Stimulation of incretin secreting cells. *Ther Adv Endocrinol Metab.* 2016; 7:24-42.
5. Collins P J, Horowitz M, Chatterton B E. Proximal, distal and total stomach emptying of a digestible solid meal in normal subjects. *Br J Radiol.* 1988; 61:12-18.
6. Tougas G, Eaker E Y, Abell T L, et al. Assessment of gastric emptying using a low fat meal: establishment of international control values. *Am J Gastroenterol.* 2000; 95:1456-1462.
7. Schwartz J G, McMahan C A, Green G M, et al. Gastric emptying in Mexican Americans compared to non-Hispanic whites. *Dig Dis Sci.* 1995; 40:624-630.
8. Horowitz M, Edelbroek M A, Wishart J M, et al. Relationship between oral glucose tolerance and gastric emptying in normal healthy subjects. *Diabetologia.* 1993; 36:857-862.
9. Perano S J, Rayner C K, Kritas S, et al. Gastric Emptying Is More Rapid in Adolescents With Type 1 Diabetes and Impacts on Postprandial Glycemia. *J Clin Endocrinol Metab.* 2015; 100:2248-2253.
10. Marathe C S, Rayner C K, Jones K L, et al. Relationships between gastric emptying, postprandial glycemia, and incretin hormones. *Diabetes Care.* 2013; 36:1396-1405.
11. Marathe C S, Rayner C K, Lange K, et al. Relationships of the early insulin secretory response and oral disposition index with gastric emptying in subjects with normal glucose tolerance. *Physiol Rep.* 2017; 5.
12. Phillips W T, Schwartz J G, McMahan C A. Rapid gastric emptying of an oral glucose solution in type 2 diabetic patients. *J Nucl Med.* 1992; 33:1496-1500.
13. Abell T L, Camilleri M, Donohoe K, et al. Consensus recommendations for gastric emptying scintigraphy: a joint report of the American Neurogastroenterology and Motility Society and the Society of Nuclear Medicine. *J Nucl Med Technol.* 2008; 36:44-54.
14. Phillips W T, Schwartz J G, Blumhardt R, et al. Linear gastric emptying of hyperosmolar glucose solutions. *J Nucl Med.* 1991; 32:377-381.
15. Kusano M, Zai H, Shimoyama Y, et al. Rapid gastric emptying, rather than delayed gastric emptying, might provoke functional dyspepsia. *J Gastroenterol Hepatol.* 2011; 26 Suppl 3:75-78.
16. Jones K L, Russo A, Stevens J E, et al. Predictors of delayed gastric emptying in diabetes. *Diabetes Care.* 2001; 24:1264-1269.
17. Maurer A H. Advancing gastric emptying studies: standardization and new parameters to assess gastric motility and function. *Semin Nucl Med.* 2012; 42:101-112.
18. Quigley E M. The pathophysiology of diabetic gastroenteropathy: more vague than vagal. *Gastroenterology.* 1997; 113:1790-1794.
19. Frank J W, Saslow S B, Camilleri M, et al. Mechanism of accelerated gastric emptying of liquids and hyperglycemia in patients with type II diabetes mellitus. *Gastroenterology.* 1995; 109:755-765.
20. Schwartz J G, Green G M, Guan D, et al. Rapid gastric emptying of a solid pancake meal in type II diabetic patients. *Diabetes Care.* 1996; 19:468-471.
21. Weytjens C, Keymeulen B, Van Haleweyn C, et al. Rapid gastric emptying of a liquid meal in long-term Type 2 diabetes mellitus. *Diabet Med.* 1998; 15:1022-1027.
22. Phillips W T, Salman U A, McMahan C A, et al. Accelerated gastric emptying in hypertensive subjects. *J Nucl Med.* 1997; 38:207-211.
23. Talley N J, Ford A C. Functional Dyspepsia. *N Engl J Med.* 2015; 373:1853-1863.
24. Lacy B E, Weiser K T, Kennedy A T, et al. Functional dyspepsia: the economic impact to patients. *Aliment Pharmacol Ther.* 2013; 38:170-177.

25. Min Y W. The Implication of Gastric Dysmotility in the Pathophysiology of Functional Dyspepsia. *J Neurogastroenterol Motil.* 2017; 23:323-324.
26. Camilleri M. Functional Dyspepsia and Gastroparesis. *Dig Dis.* 2016; 34:491-499.
27. Delgado-Aros S, Camilleri M, Cremonini F, et al. Contributions of gastric volumes and gastric emptying to meal size and postmeal symptoms in functional dyspepsia. *Gastroenterology.* 2004; 127:1685-1694.
28. Lunding J A, Tefera S, Gilja O H, et al. Rapid initial gastric emptying and hypersensitivity to gastric filling in functional dyspepsia: effects of duodenal lipids. *Scand J Gastroenterol.* 2006; 41:1028-1036.
29. Halland M, Bharucha A E. Relationship Between Control of Glycemia and Gastric Emptying Disturbances in Diabetes Mellitus. *Clin Gastroenterol Hepatol.* 2016; 14:929-936.
30. MacGregor I L, Gueller R, Watts H D, et al. The effect of acute hyperglycemia on gastric emptying in man. *Gastroenterology.* 1976; 70:190-196.
31. Schvarcz E, Palmer M, Aman J, et al. Physiological hyperglycemia slows gastric emptying in normal subjects and patients with insulin-dependent diabetes mellitus. *Gastroenterology.* 1997; 113:60-66.
32. Quigley E M. The evaluation of gastrointestinal function in diabetic patients. *World J Gastroenterol.* 1999; 5:277-282.

What is claimed is:

1. A method of treating a subject for a condition associated with a gastric emptying disorder comprising determining whether the subject has a gastric emptying disorder using a system for classifying dyspeptic disorders and administering to the subject a medication for that gastric emptying disorder, wherein the system for classifying dyspeptic disorders comprises:

a) a scintigraphic measurement equipment configured to measure, from a subject that has ingested at a set time point a meal comprising carbohydrate and radiolabeled protein, scintigraphic data of the subject's solid gastric emptying rate at a plurality of time points over a predetermined amount of time, subsequent to the set time point;

b) a glucometric measurement equipment configured to measure, from the subject, glucometric data of the subject's blood glucose level at the plurality of time points subsequent to the set time point;

c) a computer system, comprising at least one processor and computer readable memory operatively connected to the at least one processor, which computer system is operatively connected to the scintigraphic measurement equipment and the glucometric measurement equipment, and wherein the computer system is configured to perform the steps of:

(1) storing on the memory a plurality of control values in one or more databases, wherein the plurality of control values comprise:

(A) a first set of solid gastric emptying control values, wherein each solid gastric emptying control value of the first set of solid gastric emptying control values corresponds to one time point of the plurality of time points, and wherein for a first set of time points of the plurality of time points, the first set of solid gastric emptying control values comprises at least one of (1) a predetermined upper solid gastric emptying value and (2) a predetermined lower solid gastric emptying value; and (B) a second set of blood glucose control values, wherein each blood glucose control value of the second set of blood glucose control values corresponds to one time point of the plurality of time points, and wherein for a second set of time points of the plurality of time points, the second set of blood glucose control value corresponds to at least one of (1) a predetermined upper blood glucose value, and (2) a predetermined lower blood glucose value;

(2) at each of the plurality of time points, performing the following steps:

(i) obtaining, from the scintigraphic measurement equipment, at a respective time point respective scintigraphic data for the subject, and storing said respective time point and said respective scintigraphic data in memory;

(ii) obtaining, from the glucometric measurement equipment, at the respective time point respective glucometric data for the subject, and storing said respective time point and said respective glucometric data in memory;

(iii) accessing, using the processor from memory, for at least the respective time point, at least the following respective time point information:
   a. respective scintigraphic data;
   b. respective predetermined upper solid gastric emptying value to the extent available;
   c. respective predetermined lower solid gastric emptying value to the extent available;
   d. respective glucometric data;
   e. respective predetermined upper blood glucose value to the extent available;
   f. respective predetermined lower blood glucose value to the extent available;

(iv) generating, by the computer system, first machine-readable instructions to render a first graphical user interface including a first graphical representation of:
   a. the scintigraphic data for the subject at the respective time point;
   b. the predetermined upper solid gastric emptying value at the respective time point, to the extent available; and
   c. the predetermined lower solid gastric emptying value at the respective time point, to the extent available; and (v) generating, by the computing system, second machine-readable instructions to render a second graphical user interface including a second graphical representation of:
   a. the glucometric data for the subject at the respective time point;
   b. the predetermined upper blood glucose value, at the respective time point, to the extent available; and
   c. the predetermined lower blood glucose value at the respective time point, to the extent available;

d) transmitting, by the computer system to a first electronic device, the first machine-readable instructions so as to cause the first electronic device to render the first graphical user interface on a first screen of a display associated with the first electronic device comprising a visual display of the subject's solid gastric emptying rate;

e) transmitting by the computer system to the first electronic device, the second machine-readable instructions so as to cause the first electronic device to render the second graphical user interface on a second screen of the display associated with the first electronic device comprising a visual display of the subject's blood glucose levels;

f) monitoring, by the at least one processor of the computer system, the subject's solid gastric emptying rate and of the subject's blood glucose levels to determine at least one event of a plurality of events has occurred, wherein the plurality of events includes:

(i) rapid gastric solid emptying and elevated blood glycemic excursion;

(ii) rapid gastric solid emptying and normal blood glycemic excursion;

(iii) rapid gastric solid emptying and diminished blood glycemic excursion;

(iv) delayed gastric solid emptying at 4 hours postprandial and elevated blood glycemic excursion;

(v) delayed gastric solid emptying at 4 hours postprandial and normal blood glycemic excursion;

(vi) delayed gastric solid emptying at 4 hours postprandial and diminished blood glycemic excursion;

(vii) delayed gastric solid emptying at 2 hours postprandial and elevated blood glycemic excursion;

(viii) delayed gastric solid emptying at 2 hours postprandial and normal blood glycemic excursion;

(ix) delayed gastric solid emptying at 2 hours postprandial and diminished blood glycemic excursion;

(x) normal gastric solid emptying and elevated blood glycemic excursion;

(xi) normal gastric solid emptying and normal blood glycemic excursion; and (xii) normal gastric solid emptying and diminished blood glycemic excursion;

g) transmitting, from the computer system to the first electronic device or a second electronic device, in response to the at least one processor of the computer system determining the at least one event of the plurality of events has occurred, an alert wherein the alert indicates that the subject has a dyspeptic disorder, or as having a condition associated with a dyspeptic disorder, if the at least one event is one or more of f) (i) through f) (xi), and wherein the alert indicates that the subject does not have a dyspeptic disorder or a condition associated with a dyspeptic disorder if the at least one event is f) (xii), wherein the alert is unique for each of one of eleven different categories of dyspeptic disorder, or of the condition associated with a dyspeptic disorder.

2. The method of claim 1, wherein the subject is determined to have a gastric emptying disorder which is a functional dyspepsia that should not be treated with a pro-motility therapeutic, as indicated in events f(i)-f(iv), f(vii) and f(x)-f(xii), and wherein the medication administered comprises pramlintide or a GLP-1 agonist.

3. The method of claim 2, wherein the subject is determined to have a gastric emptying disorder which is a functional dyspepsia that should be treated with a pro-motility therapeutic, as indicated in f(v)-f(vi), f(viii)-f(ix), and f(xi)-f(xii), and wherein the medication administered comprises a pro-motility therapeutic.

4. The method of claim 3, wherein the pro-motility therapeutic is a cholinergic agonist, prokinetic agent, or opioid antagonist.

5. The method of claim 1, wherein the subject is determined to have a gastric emptying disorder which is a functional dyspepsia that should not be treated with a pro-motility therapeutic, as indicated in events f(i)-f(iv), f(vii) and f(x)-f(xii), and wherein the medication administered comprises a soluble fiber.

6. The method of claim 1, wherein the subject is determined to have a gastric emptying disorder which comprises an elevated blood glycemic excursion, as indicated in events f(i), f(iv), f(vii), and f(x), and wherein the medication administered comprises pramlintide, metformin, or an oral protease inhibitor.

7. The method of claim 1, wherein the subject is determined to have a gastric emptying disorder which comprises an elevated blood glycemic excursion, as indicated in events f(i), f(iv), f(vii), and f(x), and wherein the medication administered comprises a treatment which attenuates development of diabetes, hypertension, obesity or metabolic syndrome.

* * * * *